United States Patent
Graubner et al.

(10) Patent No.: US 11,618,913 B2
(45) Date of Patent: Apr. 4, 2023

(54) METHOD FOR PREPARING XYLOGLUCAN-OLIGOSACCHARIDES

(71) Applicant: TECHNISCHE UNIVERSITÄT MÜNCHEN, Munich (DE)

(72) Inventors: Sigrid Graubner, Munich (DE); Vladimir Zverlov, Munich (DE); Wolfgang Schwarz, Munich (DE); Petra Eichinger, Unterschleissheim (DE); Björn Andreessen, Freising (DE); Jonathan Herlet, Wolfratshausen (DE); Matthias Mechelke, Munich (DE); Philipp Schulte, Munich (DE); Wolfgang Liebl, Freising (DE)

(73) Assignee: TECHNISCHE UNIVERSITÄT MÜNCHEN, Munich (DE)

( * ) Notice: Subject to any disclaimer, the term of this patent is extended or adjusted under 35 U.S.C. 154(b) by 189 days.

(21) Appl. No.: 16/765,906

(22) PCT Filed: Nov. 16, 2018

(86) PCT No.: PCT/EP2018/081577
§ 371 (c)(1),
(2) Date: May 21, 2020

(87) PCT Pub. No.: WO2019/101648
PCT Pub. Date: May 31, 2019

(65) Prior Publication Data
US 2020/0362379 A1    Nov. 19, 2020

(30) Foreign Application Priority Data
Nov. 22, 2017 (EP) ..................... 17203087

(51) Int. Cl.
*C12P 19/14*  (2006.01)
(52) U.S. Cl.
CPC ....... *C12P 19/14* (2013.01); *C12Y 302/01151* (2013.01)
(58) Field of Classification Search
CPC ........................ C12P 19/14; C12Y 302/01151
See application file for complete search history.

(56) References Cited

U.S. PATENT DOCUMENTS 10,294,484 B2 * 5/2019 Brevnova .............. C12N 15/81

FOREIGN PATENT DOCUMENTS

| JP | 2011019429 | 2/2011 |
| WO | 1991/011112 | 8/1991 |

OTHER PUBLICATIONS

Bachmann S L et al, "Purification and Cooperative Activity of Enzymes Constituting the Xylan-Degrading System of Thermomonospora Fusca", Applied and Environmental Microbiology, American Society for Microbiology, US,vol. 57, No. 8, Aug. 1, 1991 (Aug. 1, 1991), pp. 2121-2130.
V. V. Zverlov, "Two new major subunits in the cellulosome of Clostridium thermocellum: xyloglucanase Xgh74A and endoxylanaseXyn10D", Microbiology,vol. 151, No. 10, Oct. 1, 2005 (Oct. 1, 2005), pp. 3395-3401.
Berezina Oksana V et al, "Thermostable multifunctional GH74 xyloglucanase from Myceliophthora thermophila: high-level expression in Pichia pastoris and characterization of the recombinant protein", May 5, 2017 (May 5, 2017), vol. 101, No. 14, pp. 5653-5666.
Song Shuang et al, "Characterization of two novel family 12 xyloglucanases from the thermophilic Rhizomucor miehei", Mar. 6, 2013 (Mar. 6, 2013), vol. 97, No. 23, pp. 10013-10024.
Dominic D W S Wong et al, "A novel xyloglucan-specific endo-beta-1,4-glucanase: biochemical properties and inhibition studies", Applied Microbiology and Biotechnology, Springer, Berlin, DE,vol. 86, No. 5, Dec. 29, 2009 (Dec. 29, 2009), pp. 1463-1471.
"Endoglucanase D, gene celD.Clostridium thermocellum (strain ATCC 27405 / DSM 1237 / NBRC 103400 / NCIMB 10682 / NRRL B-4536 / VPI 7372) (Ruminiclostridium thermocellum)", UniProtKB17 Apr. 2007 (Apr. 17, 2007), Database accession No. A3DDN1.
Daniela E. Koeck et al., "*Herbivorax saccincola* gen. nov., sp. nov., a cellulolytic, anaerobic, thermophilic bacterium isolated via in sacco enrichments from a lab-scale biogas reactor", International Journal of Systematic and Evolutionary Microbiology,vol. 66, No. 11, Nov. 1, 2016 (Nov. 1, 2016), pp. 4458-4463.
"Endoglucanase E, gene celE5. Herbivorax saccincola", UniProtKB25 Apr. 2018 (Apr. 25, 2018), Database accession No. A0A2K9E379.
Meera E. Atreya et al., "Alleviating product inhibition in cellulase enzyme Cel7A", Biotechnology and Bioengineering,vol. 113, No. 2, Feb. 1, 2016 (Feb. 1, 2016), pp. 330-338.

* cited by examiner

*Primary Examiner* — Maryam Monshipouri
(74) *Attorney, Agent, or Firm* — JMB Davis Ben-David

(57) ABSTRACT

The present invention relates to a method for preparing oligosaccharides which can be used among others as food additives to reduce calorie content, to sweeten food products, to increase the fiber content of food products, to improve the texture of food products and to stimulate the gut microbiome bacteria. Furthermore they can be applied in the fields of animal feed, or other applications. More particularly, this invention is directed to a high temperature hydrolysis of xyloglucan polysaccharide to defined xyloglucan oligosaccharides. The invention further relates to oligosaccharide hydrolysates produced with the method of the invention and to the use of said oligosaccharide hydrolysates in human and/or animal nutrition, as prebiotic or other uses. Further provided are novel endoglucanases for use in the method of the invention as well as in other applications.

8 Claims, 6 Drawing Sheets
Specification includes a Sequence Listing.

SEQ ID 3

METHOD FOR PREPARING XYLOGLUCAN-OLIGOSACCHARIDES

CROSS-REFERENCE TO RELATED APPLICATIONS

This is the U.S. National Stage of International Patent Application No. PCT/EP2018/081577 filed on Nov. 16, 2018, which in turn claims the benefit of European Patent Application No. 17203087.6 filed on Nov. 22, 2017.

FIELD OF THE INVENTION

The present invention relates to a method for preparing oligosaccharides which can be used among others as food additives to reduce calorie content of food products, to sweeten food products, to increase the fiber content of food products, to improve the texture of food products and to stimulate the gut microbiome bacteria. Furthermore they can be applied in the fields of animal feed, or other applications. More particularly, this invention is directed to a high temperature hydrolysis of xyloglucan polysaccharides to defined xyloglucan oligosaccharides. The invention further relates to oligosaccharide hydrolysates produced with the method of the invention and to the use of said oligosaccharide hydrolysates in human and/or animal nutrition, as a prebiotic or for other uses. Further provided are novel endoglucanases for use in the method of the invention as well as in other applications.

BACKGROUND OF THE INVENTION

Commonly, fats, oils, starch, carbohydrates, sugars as well as products derived therefrom are utilized extensively in processed food. These ingredients have critical functional significance with regard to the appearance, taste, mouth feel and other organoleptic qualities of food. However, they can be metabolized by the human body during the intestinal passage and thus contribute significantly to the calorie content of such food. Recently, consumers have become increasingly health conscious. Thus, many individuals are attempting to minimize their intake of high-calorie food and food containing high levels of fat. Consumers are demanding reduced calorie and low-fat versions of traditional processed food. By adding non-digestible oligosaccharides, the amount of sugars and fats can be reduced without losing the organoleptic quality of processed food.

Regulatory agencies like the European Agency for Food Safety (EFSA Journal, 2010) and the American Food and Drug Agency (FDA) (https://www.accessdata.fda.gov/scripts/InteractiveNutritionFactsLabel/factsheets/Dietary_Fiber.pdf) acknowledged the importance of dietary fiber daily intake and suggested 25 g per day as a recommended intake for an average adult per day. Studies indicated however that the current average intake of dietary fiber is about 18 g per day (Hoy and Goldman, 2014). Consequently, an expanding need for food additives exists to functionally substitute for the calorie/fat-imparting content of processed food by increasing fiber content without adversely affecting the organoleptic quality. The invention solves the problem to provide an additive which meets the aforementioned requirements and overcomes the obstacles of the prior art.

The patent application WO1991011112A1 describes a process of enzymatic xyloglucan hydrolysis to oligosaccharides at a temperature between 45-50° C. with the enzyme being added at high concentrations. Furthermore the process produces besides the desired oligosaccharides with a high degree of polymerization (DP 7-9) over 15% of small oligosaccharides and monomeric sugars, which have to be removed in a second downstream process step. Our invention carefully selects the enzyme and circumvents the production of smaller oligosaccharides and monomeric sugars in combination with an increase of process efficiency due to the high temperature.

SUMMARY OF THE INVENTION

The invention solves the problem by the method of claim 1. It was surprisingly found that a high temperature hydrolysis of a xyloglucan source such as tamarind kernel powder, provides a low-calorie food additive, which can be used to replace the presently calorie-imparting content of processed food while increasing the fiber content without adversely affecting the organoleptic quality. Further surprisingly, it was discovered that using a high temperature procedure and enzymes with a high temperature profile simplifies xyloglucan-polysaccharide hydrolysis, improves overall performance and avoids additional purification procedures. The method of the invention can be performed with one enzyme only, because the specific, carefully selected enzyme exhibiting xyloglucanase activity at a temperature higher than 50° C. is sufficient to completely hydrolyze the xyloglucan-polysaccharide even at high substrate amounts of 700 g/l or higher.

Said enzyme may for example be an endoglucanase, for example be selected from an endoglucanase belonging to glycoside hydrolase (GH) family 5, 9, 12, 16, 44 or 74.

The invention further provides a bacterial enzyme having at least 75% sequence identity to a polypeptide selected from SEQ ID NO: 1 to 4. Said enzyme suitably exhibits xyloglucanase activity at temperatures higher than 50° C.

The invention further provides a bacterial enzyme having at least 75% sequence identity to a polypeptide selected from SEQ ID NO: 1 to 4, which exhibits xyloglucanase activity in the presence of high DP7-DP9 concentrations.

The invention also provides a xyloglucan hydrolysate, which is produced with the method of the invention. Said xyloglucan hydrolysate is characterized in that it substantially comprises a mixture of DP7 to DP9 xyloglucan oligosaccharides (XGOS).

The invention further relates to the use of said xyloglucan hydrolysate to produce food products. The invention also relates to the xyloglucan hydrolysate and the food products containing the same for use in human nutrition.

The invention further relates to the use of said xyloglucan hydrolysate to produce feed products. The invention also relates to the xyloglucan hydrolysate and the feed products containing the same for use in animal nutrition.

The xyloglucan hydrolysate produced with the method of the invention and the food products containing the same are also provided for use in improving human health, such as for lowering the blood glucose level after meal intake, as satiety agent or to reduce calories in food.

DETAILED DESCRIPTION OF THE INVENTION

In a preferred embodiment, the invention provides a method for producing xyloglucan oligosaccharides (XGOS) from a xyloglucan source, said method comprising the enzymatic hydrolysis of xyloglucan at a temperature higher than 50° C. by an enzyme, which exhibits a xyloglucanase activity at a temperature higher than 50° C.

The preferred xyloglucan source is a side product of food production, most preferably a product stream comprising tamarind, i.e. a product derived from tamarind, comprising fractions thereof such as tamarind kernel powder, defatted tamarind kernel powder or tamarind seeds.

Alternative xyloglucan sources in accordance with the invention are for example peppergrass, rapeseed, apples, bilberry, blueberry and olives, comprising fractions thereof especially the seeds and cell walls or any other source comprising a significant xyloglucan polysaccharide content. Significant content means a xyloglucan content higher than 5%. Carbohydrate hydrolysates of these xyloglucans performed with the method described herein comprise predominantly oligosaccharides having a degree of polymerization (DP) between 6 and 11.

The tamarind xyloglucan hydrolysate is unique in that, unlike other carbohydrate hydrolysates, it comprises predominantly (typically >65%70%, preferably >75%, more preferably >80% or >85%, most preferably >90% or >95%) of oligosaccharides having a degree of polymerization (DP) between 7 and 9.

Tamarind polysaccharide is obtained from the seed of the tamarind tree, *Tamarindus indica* (subfamily Caesalpinioideae, family Fabaceae), a common forest tree probably originating from tropical Africa, which is widely cultivated in drier areas of the tropics and subtropics (mainly South- and Eastasia, Southamerica, Mediterranean), primarily in India, Burma, Bangladesh and Sri Lanka. Tamarind forms indehiscent legume fruits, 10-15 cm long pods containing the seeds which consist of about 55% pulp, 34% seed (containing 65% xyloglucan polysaccharide), and 11% shell and fiber. Tamarind seeds are a commercial source of gum and has found many commercial applications including food. In 1988, India alone produced 300.000 tons of tamarind per year (Kumar and Bhattacharya, 2008) which translate to approximately 100.000 tons tamarind seed and over 66.000 tons of xyloglucan respectively.

In a preferred embodiment of the invention, the enzyme, which exhibits a xyloglucanase activity, is an endoglucanase. More preferably, said endoglucanase has an activity profile above 50° C. This has the advantage that the xyloglucan polysaccharide, such as tamarind polysaccharide, is efficiently hydrolyzed to produce an oligosaccharide mixture comprising DP7, DP8 and DP9 oligosaccharides. Other advantages of the high temperature are the elevated solubility of the xyloglucan source and avoiding microbial contamination.

Xyloglucan is a polysaccharide consisting of a beta-glucan backbone which is composed of cellotetraose units (four beta-1,4-linked D-glucopyranose residues) whereby, seen from the non-reducing end of the saccharidic chain, the first three glucosidic residues are in the C6-position linked with a glycosidic bond to the C1-position of an alpha-D-xylopyranosidic residue; the second and/or third xylose residue may be again bound in the C2-position to the C1-position of a beta-D-galactopyranosidic residue. The fourth glucosidic residue is undecorated.

Hydrolysis of tamarind xyloglucan generates oligosaccharides DP7: XXXG, DP8: XXLG and XLXG and DP9: XLLG, whereby G designates an undecorated backbone glucose residue, X a backbone glucose residue decorated with xylose, and L a backbone glucose residue decorated with xylose and galactose; letter code naming convention from Fry et al. (1993) as summarized in FIG. 1. In some cases, rarely within tamarind xyloglucan and more often in xyloglucan from other plant sources, the sidechains are slightly different and may result in products different from those described in FIG. 1: one of the xylosidic residues in each tetramer, in most cases on the third glucose residue, may be missing, leading to a different composition of the resulting oligosaccharides depending on the hydrolytic preference of the splitting enzyme; the galactosidic residue may be replaced by an alpha-L-arabinofuranosidic residue or further decorated with different sugar residues such as another galactosidic or a L-fucopyranosidic residue; the backbone glucosidic residue may also be decorated with an alpha-L-arabinofuranosidic residue instead of the xylose; the xylosidic residue may also be connected in beta-configuration. Often the sugar residues are O-acetylated. Furthermore, rarely within tamarind xyloglucan and in xyloglucan from other sources, one of the three xylose-decorated glucose backbone residues may be in the C2 position decorated in addition with an alpha-L-arabinosidic residue (Vincken et al., 1996).

Xyloglucan hydrolyzing enzymes are rare; hydrolysis, however, is performed by a variety of enzyme types with different cleaving specificity, almost all of them at the reducing end of the non-decorated glucosidic residue. The side chains in xyloglucan protect the polymer to a certain extent from rapid degradation, due to the scarcity of the side-chain-cleaving activities in the environment and the need of a distinct activity for each of the different side chain sugars.

The glycosidic sugar bonds within the xyloglucan polymer can be cleaved by certain hydrolytic enzymes. Such enzymes, called hydrolases, cleave the glycosidic bond by addition of a water molecule in a reaction, which can be written as: $A-B+H_2O \rightarrow A-OH+B-H$, whereby A and B are sugar molecules. These hydrolytic enzymes are specific for the type of the sugar involved as well as for the type of the bond, whereby a beta-1,4-link between two glucose molecules is split by an enzyme with a beta-1,4-glucanase activity. When this enzyme is splitting any beta-1,4-glucosidic bond within a long polymeric molecule (such as it exists in the backbone of xyloglucan) in a statistic manner, this enzyme is called an endoglucanase (e.g. one type of cellulases). Endoglucanases are typically active only when two or more contiguous glucose residues within the polymer are unsubstituted (such as in cellulose). However, only every $4^{th}$ residue of the tamarind xyloglucan backbone is unsubstituted so that most endoglucanases (for instance those in most commercial cellulase preparations) are inactive on tamarind xyloglucan. Those special endoglucanases (mostly in glycoside hydrolase families GH5 and GH9) with activity on tamarind xyloglucan have to be experimentally selected; they degrade a beta-1,4-glucosidic bond on either side of the unsubstituted glucoside residue even though the other glucose residue is substituted. In addition, specific endoglucanases comprised in some other hydrolase families, e.g. GH12, GH16, GH44 or GH74, are able to degrade xyloglucan.

In addition to the enzyme activity on xyloglucan, a suitable enzyme to reach complete hydrolysis even at high substrate amounts of 70% (wt/vol) or higher resulting in high oligosaccharide concentrations is characterized by a favorable end product inhibition profile. Wong et al., 2010 characterized a GH5 endoglucanase which is linear non-competitive inhibited by XXXG oligosaccharide with a Ki of 1.46±0.13 mM. Enzymes with a more suitable end product inhibition profile Ki of 5 mM or higher can be found in GH families comprising GH5, GH9, GH12, GH16, GH44 and GH74.

In a preferred embodiment of the method of the invention, high temperature conversion of xyloglucan, such as the tamarind polysaccharide, to a hydrolysate comprising predominately DP7-DP9 oligosaccharides is accomplished by the action of an endoglucanase selected from the hydrolytic exoenzymes of bacterial or fungal origin. The enzymatic hydrolysis can be accomplished in aqueous solution containing tamarind polysaccharide over a wide range of polysaccharide concentrations. Thus, the reaction can be performed by dissolving tamarind polysaccharide in aqueous solution at a concentration from about 1% by weight up to a concentration limited only by polysaccharide solubility and solution viscosity.

A suitable endoglucanase can be selected from a wide variety of bacterial and fungal origins. It may also be derived from metagenomic DNA. Genes of selected endoglucanases are cloned in a suitable test expression system comprising strains of *E. coli, Bacillus* sp. and *Thermus thermophilus,* and expressed therein. The individual enzymes are then tested for the desired tamarind polysaccharide hydrolysis, leading to the generation of, preferably, DP7-DP9 oligosaccharides. Preferred endoglucanase genes are preferably selected and isolated from DNA obtained from thermophilic microorganisms or metagenomic DNA. Thermophilic microorganisms are those with an optimum growth range above 42° C. (Lengeler et al.). Those genes include thermostable enzymes from a group of bacteria comprising the bacterial genera *Acidothermus, Caldicellulosiruptor, Caldithrix, Clostridium, Deinococcus, Herbinix, Herbivorax, Ignavibacterium, Lachnoclostridium, Meiothermus, Rhodothermus, Thermanaeromonas, Thermanaerovibrio, Thermoanaerobacter, Thermoanaerobacterium, Thermobacillus, Thermobifida, Thermobispora, Thermomonospora, Thermosediminibacter,* and *Thermotoga.*

In many cases, extracellularly produced enzymes derived from mesophilic bacteria may have a high stability even at high temperatures and are potentially suitable to be employed in the method of the invention. Another method to select the appropriate endoglucanase is therefore to select an enzyme derived from a mesophilic or psychrophilic microorganism. Mesophilic microorganisms grow best between 20 and 42° C., and psychrophilic microorganisms grow below 20° C. (Lengeler et al.). Such endoglucanases shall be encompassed by the present invention.

Moreover, the enzyme activity of an endoglucanase, e.g. an endoglucanase derived from mesophilic bacteria, can be improved toward higher temperature by genetic engineering. Therefore, another method to select the appropriate endoglucanase is to select an enzyme derived from a mesophilic or even a psychrophilic microorganism and to improve the enzyme activity thereof toward higher temperature by genetic engineering. Such endoglucanases shall be encompassed by the present invention.

An endoglucanase belonging to GH families 5, 9, 12, 16, 44 or 74 may be derived from a mesophilic or psychrophilic microorganism, such as a mesophilic or psychrophilic bacterium belonging to the group of genera comprising *Acaryochloris, Acetivibrio, Acetoanaerobium, Acidipropionibacterium, Acidobacterium, Actinoalloteichus, Actinoplanes, Actinopolymorpha, Actinosynnema, Aeromonas, Agrobacterium, Agrococcus, Alcaligenes, Algoriphagus, Alicyclobacillus, Aliivibrio, Alistipes, Alkaliphilus, Alkalitalea, Allokutzneria, Altererythrobacter, Alteromonas, Amphibacillus, Amycolatopsis, Anabaena, Anaeromyxobacter, Aquiflexum, Arachidicoccus, Archangium, Armatimonadetes, Arsenicicoccus, Arthrobacter, Arthrospira, Asticcacaulis, Auraticoccus, Aureimonas, Bacillus, Bacteroides, Barnesiella, Bdellovibrio, Beutenbergia, Bifidobacterium, Blastochloris, Blastococcus, Blautia, Bosea, Bradyrhizobium, Brevundimonas, Brucella, Burkholderia, Butyrivibrio, Calothrix, Catenulispora, Caulobacter, Cedecea, Cellulomonas, Cellulophaga, Cellulosilyticum, Cellulosimicrobium, Cellvibrio, Chamaesiphon, Chitinophaga, Chloroflexus, Chondrocystis, Chromobacterium, Chthonomonas, Clavibacter, Clostridium, Cnuibacter, Collimonas, Colwellia, Conexibacter, Coprococcus, Corallococcus, Crinalium, Croceicoccus, Curtobacterium, Cyanobium, Cyanothece, Cyclobacterium, Cylindrospermum, Cytophaga, Dehalobacter, Dehalogenimonas, Desulfohalobium, Desulfotomaculum, Desulfovibrio, Dickeya, Dictyoglomus, Draconibacterium, Dyadobacter, Dyella, Echinicola, Emticicia, Ensifer, Enterobacter, Escherichia, Eubacterium, Fermentimonas, Fibrella, Fibrisoma, Fibrobacter, Filimonas, Fimbriimonas, Flammeovirga, Flavisolibacter, Flavobacterium, Formosa, Frankia, Fremyella, Frondihabitans, Fuerstia, Fusobacterium, Geitlerinema, Gemmatimonas, Gemmatirosa, Glaciecola, Gloeobacter, Gloeocapsa, Glutamicibacter, Gordonia, Gramella, Granulicella, Granulosicoccus, Grimontia, Gynuella, Hahella, Haliscomenobacter, Halorhodospira, Herpetosiphon, Hirschia, Hoeflea, Hoyosella, Hymenobacter, Hyphomicrobium, Isoptericola, Isosphaera, Janthinobacterium, Jeongeupia, Jiangella, Jonesia, Kibdelosporangium, Kineococcus, Kiritimatiella, Kitasatospora, Klebsiella, Kribbella, Kutzneria, Labilithrix, Lacimicrobium, Lactococcus, Lacunisphaera, Leadbetterella, Leifsonia, Lentzea, Leptolyngbya, Leptotrichia, Listeria, Lutibacter, Lysobacter, Mahella, Maribacter, Maricaulis, Marmoricola, Megamonas, Melioribacter, Mesorhizobium, Methylobacterium, Microbacterium, Microbulbifer, Microcoleus, Microlunatus, Micromonospora, Minicystis, Mitsuaria, Moorea, Mucilaginibacter, Mycobacterium, Myxobacter, Myxococcus, Nakamurella, Niabella, Niastella, Nitrospirillum, Nocardiopsis, Nonomuraea, Nostoc, Novosphingobium, Ochrobactrum, Oscillatoria, Paenarthrobacter, Paenibacillus, Paludibacter, Paludisphaera, Pandoraea, Pantoea, Parabacteroides, Paraoerskovia, Pectobacterium, Pediococcus, Pedobacter, Pelosinus, Peptoclostridium, Peptoniphilus, Phaeobacter, Photobacterium, Phycisphaera, Planctomyces, Plantibacter, Plautia, Plesiomonas, Polaribacter, Polyangium, Pontibacter, Prevotella, Proteiniphilum, Pseudarthrobacter, Pseudoalteromonas, Pseudomonas, Pseudopedobacter, Pseudopropionibacterium, Pseudoxanthomonas, Psychroflexus, Ralstonia, Raoultella, Rhizobium, Rhodobacter, Rhodococcus, Rhodovulum, Rivularia, Roseateles, Roseburia, Ruegeria, Rufibacter, Ruminiclostridium, Ruminococcus, Runella, Saccharophagus, Saccharothrix, Salegentibacter, Salinispora, Sanguibacter, Scytonema, Sediminispirochaeta, Selenomonas, Shewanella, Shinella, Siansivirga, Simiduia, Sinomonas, Sinorhizobium, Solitalea, Sorangium, Sphaerochaeta, Sphingobacterium, Sphingobium, Sphingomonas, Sphingopyxis, Spirochaeta, Spirosoma, Stackebrandtia, Stanieria, Starkeya, Stenotrophomonas, Stigmatella, Streptomyces, Streptosporangium, Synechococcus, Synechocystis, Syntrophomonas, Tannerella, Teredinibacter, Terriglobus, Thioclava, Thiolapillus, Treponema, Verrucosispora, Vibrio, Xanthomonas, Zunongwangia* and any other genus comprising and/or expressing genes for a bacterial endoglucanase of families GH9, GH12, GH16, GH44 or GH74.

Alternatively, an endoglucanase belonging to GH families 5, 9, 12, 16, 44 or 74 may be derived from a group of eukaryotic cells or organisms, such as eukaryotic cells or organisms belonging to the group of eukaryotic genera comprising *Adineta, Agaricus, Allium, Alternaria, Amitermes, Ampullaria, Anoplotermes, Aplysia, Arabidopsis, Aretaon, Arthrobotrys, Arundinaria, Aspergillus, Aulone-* mia, Australoplax, Austrothelphusa, Austruca, Avena, Bambusa, Bankia, Bellamya, Bergbambos, Betula, Biomphalaria, Botrytis, Brachyelytrum, Brassica, Buergersiochloa, Camellia, Capsella, Capsicum, Cenchrus, Chamaecyparis, Cherax, Chimonocalamus, Chrysosporium, Chusquea, Citrus, Coenobita, Colocasia, Constrictotermes, Coptotermes, Corbicula, Cryptocercus, Cryptococcus, Cucumis, Dendrobium, Dendrocalamus, Dictyostelium, Dimocarpus, Diospyros, Eisenia, Entoria, Epidinium, Euastacus, Eucalyptus, Euphorbia, Eurycantha, Extatosoma, Ficus, Fragaria, Fusarium, Gecarcoidea, Geotrichum, Globitermes, Glycine, Glyptotermes, Gossypium, Grigiotermes, Guadua, Haliotis, Heloecius, Hemileia, Hevea, Hibanobambusa, Hodotermopsis, Hordeum, Hospitalitermes, Humicola, Hypocrea, Ilyograpsus, Lactuca, Leptographium, Leptosphaeria, Leucoagaricus, Lichtheimia, Lilium, Limnoria, Lotus, Macrophthalmus, Macrotermes, Magnaporthe, Malus, Mangifera, Manilkara, Mastotermes, Medauroidea, Medicago, Melanopsichium, Melocanna, Mesocentrotus, Microcerotermes, Microtermes, Mictyris, Mizuhopecten, Nannochloropsis, Nasutitermes, Neocallimastix, Neomysis, Neosarmatium, Neotermes, Nepenthes, Neurospora, Nicotiana, Nilaparvata, Odontotermes, Oikopleura, Olyra, Oryza, Otatea, Oxytenanthera, Panesthia, Panicum, Parasesarma, Penicillium, Pericapritermes, Perinereis, Persea, Peruphasma, Phakopsora, Phanerochaete, Phaseolus, Pheretima, Phyllostachys, Picea, Pinus, Piromyces, Pisum, Pleioblastus, Pleioblastus, Pleioblastus, Podospora, Populus, Populus, Porcellio, Prunus, Pseudohelice, Pseudosasa, Pyrus, Ramulus, Raphanus, Reticulitermes, Rhodotorula, Rhynchotermes, Rubus, Saccharum, Salganea, Salix, Sambucus, Sasa, Schizostachyum, Sclerotinia, Semiarundinaria, Serendipita, Sesarmoides, Sesuvium, Setaria, Shibataea, Silene, Sinocapritermes, Sipyloidea, Solanum, Sorghum, Sphaerotermes, Sporisorium, Stellaria, Subulitermes, Sucrea, Syntermes, Teleogryllus, Theobroma, Thermothelomyces, Thielavia, Timema, Tribolium, Trichoderma, Triticum, Urochloa, Ustilago, Vigna, Vitis, Xanthophyllomyces, Zea and any other genus comprising and/or expressing genes for an eukaryotic endoglucanase of families GH5, GH9, GH12, GH16, GH44 or GH74.

Hitherto known bacterial and eukaryotic genera comprising endoglucanase genes are listed in the Carbohydrate-Active enZymes Database (CAZy) database (http://www.cazy.org).

To identify and isolate DNA sequences encoding for endoglucanases, any genomic or metagenomic sequence can be screened with bioinformatical methods for in-silico transcribed reading frames with contiguous sequence similarity to amino acid sequences of endoglucanases from families GH5, GH9, GH12, GH16, GH44 or GH74. The underlying DNA sequences can be in vitro amplified by PCR using suitable template DNA, or are synthesized. The codon usage of the synthesized DNA may be adapted to that of the intended expression host. Alternatively, genomic or metagenomic DNA is fragmented by methods known in the art, ligated in a suitable way behind an expression signal into a vector-plasmid, transformed into the intended expression host and expressed in a growing culture, either after streaking on a suitable solidified medium in agar plates or in a mixture in a suitable liquid medium. The methods are well known in the art. Colonies on agar plates can be screened for hydrolytic activity by a number of methods. These include but are not restricted to including the substrate into the agar medium, into an layer on top of the agar medium before the cell are plated, or in an overlay agar which is spread on top of grown colonies. The substrates are soluble or insoluble polymeric endoglucanase substrates comprising derivatized cellulose such as carboxymethyl-cellulose (CMC), beta-glucan such as barley beta-glucan, xyloglucan, or soluble or insoluble chromogenic substrates such beta-glucan substrates such as Azo-CM-cellulose, Azo-barley beta-glucan and Azo-xyloglucan. Clearing zones from the polymeric substrates are visible after incubation either by clearing of turbidity around colonies or by staining and destaining with dyes such as Congo-red or fluorescent stilbene, or with umbelliferone derivatives; clearing zones, staining or fluorescence from the chromogenic substrates are visible after incubation by dissolvement of the insoluble material.

Liquid cultures with endoglucanase activity are identified by crashing the bacterial cells and measuring the endoglucanase activity as described below. Endoglucanase producing cells in the cultures showing activity may have to be streaked for single cell isolation as is known in the art. Isolated pure culture are rechecked for activity as described. The genes for the endoglucanases are isolated from the identified colonies or cultures by methods of DNA isolation and PCR amplification as is well known in the art.

The presence of an endoglucanase activity in liquid cultures, culture supernatants or enzyme solutions can be determined by a number of methods, examples of which are listed hereafter. Protein is detected by an antibody-based assay (such as ELISA or Western-Blot), by SDS-PAGE and Coomassie-Blue or silver staining, or by measuring protein concentration by any of suitable methods. The enzyme activity can be determined by a number of other methods, such as are described in example 2 using model substrates for endoglucanases comprising CMC, barley-beta-glucan, and xyloglucan, or chromogenic substrates containing beta-1,4-glucosidic linkages.

Endoglucanase activity is characterized by non-processive hydrolysis at the internal bonds within the beta-glucan molecule of cellulose. The points of hydrolysis are statistically distributed over the length of the substrate molecule. "Non-processive" means that the next hydrolytic action of the enzyme is not in a consecutive way at a neighboring position; the enzyme falls off the substrate and binds for the next cut at a different location of the same or another molecule, creating new cuts at any place within the polymeric molecule. Endoglucanolytic activity, also called endo-mode cellulase activity, can be determined by methods using soluble polymers comprising beta-1,4-glucan linkages such as mixed-linkage beta-glucan (beta-1,3-1,4-glucan for instance from barley or from lichen, the lichenan) or chemically modified cellulose such as hydroxyethyl- or carboxymethyl-cellulose (HEC, CMC). Examples for such methods are described hereafter.

The enzymatic activity can be quantitatively determined by the increase of reducing ends, i.e. by producing new C1-sugar ends, the reducing hemi-acetal group. These can be quantified by their reduction of chromogenic 3,5-dinitrosalicylic acid to the 3-amino-5-nitrosalicylic acid, which can be photometrically measured by its absorbance at 540 nm (Wood and Bhat 1988). An alternative method can be to hydrolyze the oligosaccharides produced by adding a beta-1,4-glucosidase and to determine the resulting monomeric glucose quantitatively in a combined enzyme assay using Hexokinase and Glucose-6-phosphate dehydrogenase in the presence of ATP and NAD. The reduced NAD (NADH+) is photometrically quantified at 340 nm. An alternative assay is the combined use of the enzymes glucose oxidase with a chromogenic determination of the formed hydrogen peroxide through peroxidase or by an electrochemical determination. A chromogen such as ortho-phenylendiamin can be used for photometrical detection. A number of commercial glucose determination assays (such as GOD/POD) are available describing both methods in detail.

A further method to determine endoglucanase activity is the reduction of viscous polymer solutions, such as from chemically modified cellulose such as HEC, CMC, or from soluble beta-glucans containing beta-1,4-glucosidic bonds such as barley mixed-linkage-glucan or lichenan. The use of CMC with a viscosimeter is a preferred method to detect specifically endoglucanase activity in a mixture with exoglucanase activity. The reduction of viscosity with time is determined. The decrease in viscosity is directly proportional to the cellulase activity and the most sensitive of the quantification methods for endoglucanase. However, enzymatic activity is relative and cannot be expressed in conventional enzymatic activity units.

Still a further method for endoglucanase activity determination is the release of oligosaccharides from chromogenically or fluorogenically derivatized dyed cellulose, cellodextrins and/or crosslinked cellulose derivatives or cellodextrins, such as AZCL-HE-cellulose, azo-alpha-cellulose, azo-Avicel, RedCL-HE-cellulose, 4,6-O-benzylidene-2-chloro-4-n itrophenyl-beta-3,1-cellotriosyl-β-glucopyranoside, 4,6-O-(3-ketobutylidene)-4-nitrophenyl-beta-D-cellopentaoside or 4,6-O-Benzylidene-4-methylumbelliferyl-beta-cellotrioside as described by McCleary et al. (1980) or Mangan et al., (2016). Such substrates release either a stained oligosaccharide which is soluble, sometimes differentiated by addition of a certain concentration of ethanol to precipitate the polymer, or a chromophore or fluorophore containing substrate. The soluble products of the enzymatic reaction can be determined by photometry or fluorometry. For some assays a beta-glucosidase has to be added. A number of commercial endoglucanase determination assays are available describing the methods in detail.

An increased activity profile regarding the enzyme activity at temperatures higher than 50° C. can e.g. be achieved by mutagenesis of endoglucanases with a suitable product distribution. Suitably, endoglucanases, which are derived from mesophilic or psychrophilic organisms are subjected to mutagenesis. The person skilled in the art knows the principle techniques of introducing mutations into enzymes in order to optimize the enzyme characteristics. Example mutations are the introduction of cysteine residues into the amino acid sequence, which form a disulfide bridge to stabilize the enzyme against thermal denaturation. In another aspect, thermal stability could be achieved by random, targeted mutagenesis or directed evolution, whereby one or several amino acids of the original amino acid sequence are substituted by amino acids differing from the original sequence. In another aspect, deletion or insertion of amino acids, loop regions or protein domains in the original amino acid sequence could be performed in order to increase thermal stability of the enzyme. In another aspect, thermostabilization of the enzyme may be achieved by encapsulation, chemical cross linking of the enzyme and addition of stabilizing compounds. Such stabilizing compounds are for example BSA, glycerol and sorbitol. Other methods to stabilize enzymes is chemical cross-linking or any other method, which leads to a suitable enzyme activity above 50° C.

Accordingly, in a preferred embodiment, the endoglucanase with enzyme activity above 50° C., which is used in the method of the invention, is derived from a eukaryotic organism or a microorganism, such as a bacterium or fungus, more preferably a microorganism, most preferably a bacterium.

In a further preferred embodiment, the endoglucanase with enzyme activity above 50° C., which is used in the method of the invention, is derived from a thermophilic microorganism, such as a thermophilic bacterium, or is thermostabilized by genetic engineering.

"Derived" according to the present invention means that an endoglucanase of interest is isolated from a wild-type organism following standard techniques, which are well known to the person skilled in the art. "Derived" also includes the recombinant production of an endoglucanase of interest in a suitable host or host cell.

In a preferred embodiment, the endoglucanase with enzyme activity at temperatures higher than 50° C. is characterized by a favorable oligosaccharide end product inhibition constant (Ki) equal to or higher than 5 mM. The endoglucanase can be produced in state of the art production hosts. However, some production hosts express, in addition to the target endoglucanase, endogenous enzymes, which may exhibit unwanted endogenous xyloglucanase enzyme activities. Such unwanted endogenous enzyme activities could lead to an enhanced hydrolysis, unwanted hydrolysis side products or unwanted transglycosylation of oligosaccharides. Enhanced hydrolysis or transglycosylation could for example result in an increased amount of smaller oligosaccharides, increased amount of monosaccharides, a more heterogeneous distribution of oligosaccharides or an unsuitable oligosaccharide distribution, thereby reducing the yield of the targeted DP7-DP9 XGOS. It is therefore advisable to test the suitability of the production host to avoid unwanted xyloglucan degradation or unwanted XGOS distribution, which leads to the reduction of the DP7-DP9 yield. In a preferred embodiment of the invention, the endoglucanase and the production host are capable of maximizing the yield of DP7-DP9 XGOS by avoiding the formation of side products. For industrial XGOS production, it is additionally preferred to use a stable and comprehensive production process of the endoglucanase. Most preferably, the endoglucanase used in the method of the invention is recombinantly produced in a bacterial host, which is devoid of any endogenous enzyme which exhibits activity on oligosaccharides, in particular on DP7-DP9 XGOS. Thereby, contamination with unwanted side activities of other enzymes can effectively be excluded.

A preferred method is to express SEQ ID 1-4 in a bacterial expression host system lacking any further enzyme activity on DP7-DP9 xyloglucan oligosaccharides.

A most preferred method is to express SEQ ID NOs 2-4 in a bacterial host system lacking any further enzyme activity on DP7-DP9 xyloglucan oligosaccharides.

A most preferred host cell is a prokaryotic cell secreting the enzyme. The prokaryotic host cell may be any Gram-positive bacterium or a Gram-negative bacterium.

Gram-positive bacteria include, but are not limited to, the group of genera comprising *Bacillus, Streptococcus, Streptomyces, Staphylococcus, Enterococcus, Lactobacillus, Lactococcus, Clostridium, Geobacillus, Oceanobacillus, Paenibacillus* and closely related bacteria, such as bacteria having >95% sequence identity in the 16S rRNA gene with the 16S rRNA gene of the aforementioned genera.

Gram-negative bacteria include, but are not limited to the genera *Escherichia, Pseudomonas, Salmonella, Campylobacter, Helicobacter, Flavobacterium, Fusobacterium, Ilyobacter, Neisseria, Thermus,* and *Ureaplasma*.

The bacterial host cell may be any *Bacillus, Paenibacillus* or *Geobacillus* cell. Suitable *Bacillus* cells for producing the endoglucanase for use in the method of the present invention include, but are not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Geobacillus stearothermophilus, Bacillus subtilis*, and *Bacillus thuringiensis* cells and closely related species, such as *Bacillus* species having >98% sequence identity in the 16S rRNA gene with the 16S rRNA gene of the aforementioned *Bacillus* species.

The bacterial host cell may also be any *Streptococcus* cell. Suitable *Streptococcus* cells for producing the endoglucanase for use in the method of the present invention include, but are not limited to, *Streptococcus equisimilis, Streptococcus pyogenes, Streptococcus uberis*, and *Streptococcus equi* subsp. *zooepidemicus* cells.

The bacterial host cell may also be any *Streptomyces* cell. Suitable *Streptomyces* cells for producing the endoglucanase for use in the method of the present invention include, but are not limited to, *Streptomyces achromogenes, Streptomyces avermitilis, Streptomyces coelicolor, Streptomyces griseus*, and *Streptomyces lividans* cells.

The bacterial host cell may also be any *Corynebacterium* cell. Suitable *Corynebacterium* cells for producing the endoglucanase for use in the method of the present invention include, but is not limited to, *Corynebacterium glutamicum* cells.

The bacterial host cell may also be any *Escherichia* cell. Suitable *Escherichia* cells for producing the endoglucanase for use in the method of the present invention include, but is not limited to, *Escherichia coli* cells.

The host cell may also be a eukaryotic cell, such as a mammalian, insect, plant, or fungal cell.

The fungal host cell may be a yeast cell. "Yeast" as used herein includes ascosporogenous yeasts (*Endomycetales*), basidiosporogenous yeasts, and yeasts belonging to the Fungi Imperfecti (*Blastomycetes*). The group of yeast host cells include, but are not limited to, *Candida, Hansenula, Kluyveromyces, Pichia, Saccharomyces, Schizosaccharomyces*, or *Yarrowia* cell.

In a preferred embodiment, the yeast host cell is selected from the group comprising a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* cell. In another preferred embodiment, the yeast host cell is a *Kluyveromyces lactis* cell. In another preferred embodiment, the yeast host cell is a *Yarrowia lipolytica* cell.

In a further preferred aspect, the fungal host cell is a filamentous fungal cell. "Filamentous fungi" include all filamentous forms of the subdivisions Eumycota and Oomycota (as defined by Hawksworth et al., 1995). The filamentous fungi are generally characterized by a mycelial wall composed of chitin, cellulose, glucan, chitosan, mannan and other complex polysaccharides. Vegetative growth occurs by hyphal elongation and carbon catabolism is obligate aerobic. In contrast, vegetative growth by yeasts such as *Saccharomyces cerevisiae* occurs by budding of a unicellular thallus and carbon catabolism may be fermentative.

In a preferred embodiment, the filamentous fungal host cell is selected from the group comprising *Acremonium, Aspergillus, Aureobasidium, Bjerkandera, Ceriporiopsis, Chrysosporium, Coprinus, Coriolus, Cryptococcus, Filibasidium, Fusarium, Humicola, Hypocrea, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cells.

In a preferred embodiment, the filamentous fungal host cell is selected from the group comprising an *Aspergillus awamori, Aspergillus fumigatus, Aspergillus foetidus, Aspergillus japonicus, Aspergillus nidulans, Aspergillus niger* or *Aspergillus oryzae* cell. In another preferred embodiment, the filamentous fungal host cell is selected from the group comprising a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In another preferred embodiment, the filamentous fungal host cell is selected from the group comprising a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

In a most preferred embodiment, an endoglucanase is used in the method of the invention, wherein said endoglucanase has at least 75% sequence identity to a polypeptide, which has an amino acid sequence selected from SEQ ID NO: 1 to SEQ ID NO: 4.

The endoglucanase according to SEQ ID NO: 1 was isolated from *Clostridium thermocellum*.

Among the most actively hemicellulose degrading bacteria, *Herbivorax saccincola* SR1 was isolated from thermophilic grass silage/cow manure biogas reactor. It grows at a temperature from 45-65° C. with an optimum temperature of 60° C. and was found to ferment xylan, xyloglucan and cristalline cellulose. *Herbivorax saccincola* was classified as a new family in the Ruminococcaceae (Koeck et al. 2016). Among the genomic sequence of the bacterium a sequence belonging to GH family 5 was identified (Pechtl et al., to be published). The reading frame has been cloned in *E. coli* and the expressed and purified gene products has been characterized. Endoglucanase of SEQ ID NO: 2 has been selected as a suitable enzyme for the purpose of this invention. Accordingly, in a particularly preferred embodiment, the endoglucanase used in the method of the invention is derived from a newly isolated microorganism *Herbivorax saccincola* DSM101079 and essentially consists of or consists of a polypeptide having at least 75% amino acid sequence identity to a new isolated polypeptide of SEQ ID NO: 2.

In a further particularly preferred embodiment, said endoglucanase comprises, essentially consists of or consists of a polypeptide having at least 75% amino acid sequence identity to a polypeptide of SEQ ID NO: 4, wherein in said endoglucanase the dockerin domain is deleted which results in a 7fold enzyme activity increase. The polypeptide of SEQ ID NO: 4 is suitably obtained from a polypeptide of SEQ ID NO: 2 by deleting the dockerin domain.

In another particularly preferred embodiment, said endoglucanase comprises, essentially consists of or consists of a polypeptide having at least 75% amino acid sequence identity to a polypeptide of SEQ ID NO: 3, wherein in said endoglucanase the dockerin domain is deleted which results in a 4fold enzyme activity increase. The polypeptide of SEQ ID NO: 3 is suitably obtained from a polypeptide of SEQ ID NO: 1 by deleting the dockerin domain.

In a further embodiment, the method of the invention comprises further processing steps of the hydrolysate. The hydrolysate can for example be processed to remove solids, salts and impurities with state-of-the-art methods. The resulting oligosaccharide solution is optionally decolorized by treatment with activated charcoal or any other decolorizing state-of-the-art method. Finally, the purified oligosaccharide mixture, which substantially comprises DP7-DP9 XGOS, can be dried by freeze or spray drying or roll-drying to provide a multi-functional food additive as a free-flowing powder, which can be formulated and packed for distribution or the purified oligosaccharide mixture is stored as concentrated liquid formulation. The remaining mixture of DP7-DP9 XGOS can partially substitute the metabolizable carbohydrate components of processed food at high levels without compromising the organoleptic qualities of the resulting food with reduced calories. Importantly, the use of the DP7-DP9 XGOS mixture in food products also allows the reduction of fat content as a flavor carrier without affecting flavor intensity.

In accordance with the present invention, a high temperature and single enzyme hydrolysis of tamarind endosperm polysaccharide is utilized to prepare a multi-functional food additive. Further in accordance with the present invention, tamarind polysaccharide is converted in high yield to a food grade hydrolysate believed to substantially comprise DP7, DP8 and DP9 XGOS using an endoglucanase with an enzyme activity profile at a temperature higher than 50° C. Typically, the endoglucanase has an activity profile at reaction temperatures in the range from 50.5 to about 80° C., preferably from 55 to 75° C., more preferably from 55 to 70° C., most preferably from 55 to 65° C.

More preferably, an endoglucanase with an activity profile at temperatures higher than 50° C. selectively hydrolyzes tamarind polysaccharide to produce an oligosaccharide mixture comprising DP7, DP8 and DP9 XGOS. Typically, enzymatic hydrolysis of tamarind polysaccharide in accordance with the present invention is continued until the majority of the xyloglucan-polysaccharide is hydrolyzed to DP7-DP9 XGOS.

In a preferred embodiment the final tamarind polysaccharide substrate amount used is equal to or more than 100 g/L, 200 g/L, 300 g/L, 400 g/L, 500 g/L, 600 g/L, 700 g/L and 750 g/L in the method of the invention.

In another preferred embodiment, 0.01%, 0.05%, 0.1%, 0.2%, 0.3%, 0.4% or 0.5% of endoglucanase in respect to xyloglucan substrate are used in the method of the invention.

In a further preferred embodiment, more than 25%, 35%, 45%, 55%, 65% and 75% or more of the tamarind polysaccharide substrate is hydrolyzed to substantially yield DP7-DP9 XGOS. "Substantially yield" in the context of the invention means that the content of DP7-DP9 XGOS as a fraction of all oligosaccharides in the hydrolysate is at least 50% or higher, preferably 60% or 70%, more preferably 75%, most preferably 80% or higher.

Further preferably, the reaction time to substantially yield DP7-DP9 XGOS is in the range of 72 h to 12 h or shorter, more preferably 72 h, or 60 h, 48 h or 36 h, most preferably 24 h, 12 h or even shorter.

In a most preferred embodiment of the method of the invention, the final xyloglucan substrate amount used is 500 g/L or higher, the enzyme concentration is below 0.05% and the hydrolysis substantially yields at least 65% DP7-DP9 XGOS in less than 24 h.

In a most preferred embodiment, the method for producing xyloglucan oligosaccharides (XGOS) from a xyloglucan source according to the present invention comprises the steps of:
  enzymatic hydrolysis of xyloglucan at a temperature higher than 50° C. by an endoglucanase which exhibits xyloglucanase activity at a temperature higher than 50° C.,
  removal of solids,
  removal of salts,
  removal of further impurities,
  optionally decolorization of the hydrolysate,
  drying of the hydrolysate by e.g. freeze or spray drying or roll-drying or storage of the hydrolysate as a concentrated liquid formulation.

The amount of endoglucanase to be used to effect the requisite hydrolysis of tamarind polysaccharide depends on the reaction conditions and the activity level of the endoglucanase. Under optimal conditions, the endoglucanase can be used at an amount as low as 0.005 wt/wt relative to the tamarind polysaccharide starting material. Typically, the concentration of the endoglucanase appropriate for production of the hydrolysate ranges from 0.005% to 0.5%, preferably 0.01% to 0.5%, more preferably 0.05% to 0.5% wt/wt relative to the tamarind polysaccharide starting material. Typical amounts of the endoglucanase used in the method of the invention are 0.01%, 0.05%, 0.1%, 0.2%, 0.3%, 0.4% or 0.5% wt/wt relative to the tamarind polysaccharide starting material. The reaction time may vary depending on the endoglucanase used and the hydrolysis conditions. Typical reaction temperatures range from 50.5 to about 80° C., preferably from 55 to 75° C., more preferably from 55 to 70° C., most preferably from 55 to 65° C.

Thus, in a further most preferred embodiment, the method for producing xyloglucan oligosaccharides (XGOS) from a xyloglucan source according to the present invention comprises the steps of:
  enzymatic hydrolysis of tamarind polysaccharide at a temperature in the range of 50.5 to 80° C. by an endoglucanase which exhibits xyloglucanase activity at a temperature in the range from 50.5 to 80° C.;
  removal of solids,
  removal of salts,
  removal of further impurities,
  optionally decolorization of the hydrolysate,
  drying of the hydrolysate by e.g. freeze or spray drying or roll-drying or storage of the hydrolysate as concentrated liquid formulation.

The steps for an embodiment of the method for producing xyloglucan oligosaccharides (XGOS) from a xyloglucan source according to the present invention are visualized in FIG. 2.

Specific Embodiments

In a more specific embodiments of the present invention, the hydrolysis of tamarind oligosaccharide can be performed as follows:

Tamarind kernel powder (TKP) or defatted TKP is dissolved in water or demineralized water at a temperature in the range of 50.5 to 70° C., preferably 50.5 to 65° C., more preferably 50.5 to 60° C., most preferably at temperature of 51° C., 52° C., 53° C., 54° C., 55° C., 56° C., 57° C., 58° C., 59° C. or 60° C. The final concentration of TKP is 1, 10, 20, 30, 40, 50, 60, 75% (wt/vol) respectively. The TKP is added to the water by stirring at the desired temperature. One example to dissolve TKP is to add the TKP in one step reaching the final TKP concentration, another example is to add the TKP periodically or continuously to attain the final TKP concentration.

The enzyme may be added at the beginning of the hydrolysis as liquid or dry formulated soluble enzyme. Another example for enzymatic hydrolysis is to immobilize the enzyme by binding to a matrix. The enzyme is dissolved in one example to the liquid before the TKP is added. In another example the enzyme is added to the dissolved TKP.

Another example is to add TKP periodically to an ongoing TKP hydrolysis reaction mixture to attain high TKP turn over and high product concentrations.

The progress of the polysaccharide hydrolysis reaction can be monitored by standard analytical techniques which have been adapted for this purpose. These are techniques such as thin layer chromatography (TLC), high performance liquid chromatography (HPLC) and its variant high performance anion exchange chromatography with pulsed amperometric detection (HPAEC-PAD), size exclusion chromatography (SEC), nuclear magnetic resonance (NMR), capillary zone electrophoresis with laser-induced fluorescence detection (CZE-LIF), matrix assisted laser desorption ionization with time-of-flight detection (MALDI-TOF) and liquid chromatography with coupled mass spectrometry (LC-MS). HPAEC-PAD can be used to investigate the oligosaccharides for this invention. HPAEC-PAD features an especially highly specific and sensitive detection, as well as the highest resolution of oligosaccharide separation and was used to create the results for the present invention in most cases. Furthermore, it does not require prior derivatization and can be performed mostly automatized. HPAEC-PAD is run at highly alkaline conditions.

The analytes expected to occur as hydrolysis products may be dissolved in water in an appropriate concentration to be used as reference standards for quantification. These include monosaccharides (obtainable from Sigma Aldrich, St. Louis, USA) except for L-(+)-arabinose and D-(+)-mannose, which can e.g. be purchased from Carl Roth GmbH & Co KG (Karlsruhe, Germany) and Serva Electrophoresis GmbH (Heidelberg, Germany), respectively.

Galacturonic and glucuronic acid can be purchased from Merck Millipore GmbH (Düsseldorf, Germany) and Sigma Aldrich. All oligosaccharides can be purchased from Megazyme (Bray, Ireland) except for cellobiose (C2), which can be purchased from Applichem GmbH (Gatersleben, Germany). D-Mannitol can be used as an internal standard (ISTD) and can be purchased from Sigma Aldrich.

For the analysis by HPAEC-PAD an ICS 3000 Dionex chromatography system from Thermo Fisher Scientific (Waltham, USA) equipped with a CarboPac™ PA1 column (4×250 mm) and a PA1-precolumn (4×50 mm) can be used. The system can be set up using PEEK tubing (0.25 mm i.d.), a GM-4 gradient mixer (2 mm), an ED amperometry cell with 0.25 μL channel volume, a pH-Ag/AgCl reference electrode, 0.002" gasket and disposable gold electrodes.

Runs were performed at a column temperature of 30° C. with an injection volume of 25 μL and a flow rate of 1 mL/min. A suitable eluent gradient for the analyte separation starts e.g. at 0 min with 100 mM NaOH and 7.5 mM sodium acetate (NaOAc). The latter can be linearly increased to 100 mM at 67.5 min while 100 mM NaOH is maintained. To wash the column, the concentration of NaOAc is increased to 650 mM with 100 mM NaOH for 4 min and subsequently re-equilibrated with 100 mM NaOH for 16.3 min after each run. The carbohydrate detection with the PAD is based on the waveform "standard carbohydrate quad" (Waveform B) which was set to 1 or 2 Hz. Prior to the analysis of the polysaccharide hydrolysates, the samples are diluted to a final XGOS concentration between 10 and 200 mg/l with double-distilled water. The degradation products can be identified by comparison to oligosaccharide standards (10-200 mg $L^{-1}$ each) as listed above.

Analysis of the hydrolysates by TLC can be used for quick analysis of multiple samples in parallel. TLC can e.g. be performed using silica gel 60 plates from Merck Millipore GmbH (Duesseldorf, Germany) as stationary and acetonitrile-water 8:2 v/v as mobile phase. For staining, the plates are sprayed with 5 mL staining solution (100 mL acetone, 1 g diphenylamine, 1 mL anilin) with 0.5 mL 85% freshly added phosphoric acid. Spraying can be done using the DESAGA ChromaJet DS 20 from Sarstedt (Nürmbrecht, Germany). Subsequently, the plates are developed for 20 min at 120° C. The applied volume for each hydrolysate and negative control is e.g. 4.5 μL and 1 μL of a 1 μg/μL stock solution for each analyte.

The hydrolysis product comprising the DP7-DP9 XGOS can be isolated from the hydrolysis reaction mixture by centrifugation, sedimentation or decanting. If necessary, protein components in the hydrolysate solution can be denaturated (=inactivated) by heating the reaction mixture to a temperature of at least 90° C., preferably between about 95° C. and 100° C. Denatured protein components can thereafter be removed from the hydrolysate solution by sedimentation, decanting or filtering. Remaining soluble proteins in the supernatant can be removed by applying the hydrolysate solution to conventional filter techniques or by contacting the hydrolysate solution with any commercially available ion exchange resin. This can be accomplished, for example, either by slurrying the hydrolysate solution with the resin and filtering, or by passing the hydrolysate solution through a column packed with the ion-exchange resin. Another step, which is desirable but not always necessary for processing the hydrolysate solution, is treating the hydrolysate solution with activated charcoal. This may be accomplished by adding activated charcoal, usually in an amount equal to about 5 to 20% of the weight of the dissolved hydrolysate, to the hydrolysate solution, heating the hydrolysate solution and thereafter subjecting the hydrolysate solution to a filtering step, preferably by use of a filter aid such as celite. Such treatment is effective to decolorize the hydrolysate solution and to reduce the concentration of organic impurities.

The crude carbohydrate hydrolysate can be isolated from the processed hydrolysate solution using standard carbohydrate isolation techniques e.g. by solution drying techniques, preferably lyophilization or spray drying, or by precipitation with a solute, more preferably an alcohol, most preferably ethanol, followed by filtration, wherein filtration can include membrane filtration. These procedures may have additional effects, such as decolorization and/or sterilization. Selective short chain alcoholic precipitation of the hydrolysate oligosaccharides can be used to provide a hydrolysate product comprising, consisting essentially of or consisting of DP7-DP9 XGOS. Furthermore, the same result can be achieved by employing ultra- or nanofiltration techniques or by using (sequential) simulated moving bed chromatography.

After the reaction the hydrolysate oligosaccharides (XGOS) may be separated from non-polysaccharide material. Examples for physical separation are sedimentation and filtration. Separation can take place by plain sedimentation or settling, tangential flow filtration equipped with fiber, fabric or membrane filters, filtration employing granular media, rapid rate filters or slow sand filters, or porous ceramic filters. Other examples for separation are chemical methods like coagulation, flocculation and precipitation.

Purification of the XGOS-containing hydrolysate may be achieved by adsorption processes with adsorbents such as clay, charcoal, or activated carbon, ion exchange processes with synthetic or organic polymeric resins and chelating resins, solvent precipitation with short chain alcohols, electro dialysis, and drying. Furthermore membrane processes including microfiltration, ultrafiltration, nanofiltration, reverse osmosis, and dialysis utilising synthetic membranes can be used in purification steps.

The product XGOS mixture is typically isolated as a dry, free flowing, white to cream colored powder. Alternatively, the processed hydrolysate solution or a concentrated DP7-DP9 syrup can itself be used as a food or feed additive for directly introducing the XGOS mixture into processed food recipes.

The method of the invention has the advantage that the tamarind polysaccharide, which is processed with an endoglucanase, yields a product comprising, consisting essentially of or consisting of DP7 to DP9 XGOS. In a preferred embodiment, the yield from the theoretically achievable oligosaccharides of DP7-DP9 XGOS is at least 50% or higher, preferably 60% or 70%, more preferably 75%, most preferably 80% or higher. In a further embodiment, the monosaccharide content in said product, i.e. the XGOS mixture produced with the method of invention, is below 5%, preferably below 4% or 3%, more preferably below 2%, most preferably below 1%, such as 0.9%, 0.8% 0.7%, 0.6%, 0.5% or even lower. Accordingly, the method of the invention is economical, because no further separation or removal of oligosaccharides smaller than DP7; or removal of monosaccharides is required. Solids, salt and coloring agents are separated and removed by established technologies such as chromatography or adsorption.

The invention further relates to a XGOS-containing hydrolysate as obtainable by the method of the invention, in particular to a XGOS-containing hydrolysate comprising, substantially comprising or consisting of DP7-DP9 XGOS. The XGOS mixture prepared according to the method of the invention is an odorless syrup or powder, depending on the production process. The taste is sweet with no significant other aftertaste. The XGOS mixture prepared according to the method of the invention is stable against acid degradation and heat. Moreover, the XGOS mixture prepared according to the method of the invention exhibits in vitro metabolic stability.

In accordance with the present invention, there is provided a process for preparing a XGOS mixture comprising, substantially comprising or consisting of DP7-DP9 XGOS produced by high temperature enzymatic hydrolysis of the tamarind xyloglucan polysaccharide. The product tamarind hydrolysate has been found to exhibit exceptional food-functional characteristics when used as a substitute for at least a portion of the metabolizable carbohydrate components of processed foods. Thus in another embodiment of the present invention, there is provided a processed food product wherein at least a portion of its normal metabolizable sweetening carbohydrate content is substituted or replaced by the XGOS mixture prepared with the method of the invention, in particular prepared from hydrolyzing tamarind oligosaccharide. Typically, about 1 to about 2 parts, preferably 1 to 2 parts of the XGOS mixture of the invention are replacing each part of metabolizable carbohydrate in a conventionally processed food.

Uses

A variety of uses for the isolated tamarind seed polysaccharide have been described (see Rao and Srivastava, 1973). The polysaccharide has the ability to form jellies with sugar concentrates over a wide pH range. It has also been used in food as a stabilizer in ice creams and mayonnaise. Further, the textile industry has employed tamarind polysaccharide for sizing, finishing and printing cotton and artificial silk. In the cosmetics industry, tamarind polysaccharide has been used for preparing emulsions of essential oils, shaving creams and dentifrices. It has also found use as a binder in the manufacture of compressed pills and tablets, as an excipient in making greaseless ointments and as a gelling agent in the preparation of colloidal iodine jelly.

The tamarind polysaccharide hydrolysate can be used, in accordance with the present invention, as a functional substitute for the metabolizable carbohydrate content of processed foods to provide reduced-calorie processed food products. It has been found that a composition comprising DP7-DP9 XGOS provided through endoglucanase hydrolysis of tamarind polysaccharide can substitute as much as 60% of the metabolizable carbohydrates in processed food without adversely affecting organoleptic quality of the modified food products. Moreover, the use of such oligosaccharide composition in processed foods allows, as well, a reduction in fat content without noticeable effect on food quality. More particularly, it is known, e.g. from WO 91/11112 A1, that when the tamarind hydrolysate (DP7-DP9 oligosaccharides) is substituting about 10 to about 40% of the carbohydrates in a processed food composition, fat content can be reduced by as much as 25%. Thus, use of the tamarind hydrolysate as a carbohydrate substitute in processed foods enables a significant reduction in calorie content. Significantly, too, the hydrolysate has a more homogeneous composition (a significant percentage by weight of DP7-DP9 XGOS) than other art-recognized carbohydrate hydrolysates—its functional performance is therefore highly predictable in a wide variety of processed food products. Another advantage of the tamarind polysaccharide hydrolysate prepared with the method of the invention, which comprises, consists essentially of or consists of DP7-DP9 XGOS, is, that unlike art-recognized food additive gums, the polysaccharide hydrolysate can be used at high levels in processed foods without adversely affecting the processing thereof due to its high viscosity.

The tamarind derived DP7-DP9 XGOS mixture produced with the method of the invention can be used in accordance with this invention to produce calorie-reduced food products such as candy, chewing gum, dry cake and cookie mixes, frozen dairy desserts, creams, nutritional bars, gelatin desserts, puddings, baked goods and spoonable dressings. Further, it may be employed as a bulking agent without significant increase in batter/product viscosity. The mixture has been found to dissolve quickly in water to give clear, almost colorless solutions. It can be used as a non-caloric carrier for synthetic sweeteners. When mixed with synthetic sweeteners and added either to ice tea or hot coffee, the dissolution of the product is instantaneous. Moreover, the tamarind derived XGOS hydrolysate can act as a sweetness intensifier. A baked cookie of high quality can be prepared by substituting the hydrolysate for about 10 to about 40% of the sugar called for on the original cookie recipe. In another application, the tamarind derived XGOS hydrolysate is combined with dry milk solids to produce a coffee whitener.

Accordingly, in one embodiment, the invention provides the use of the XGOS mixture comprising, consisting essentially of or consisting of DP7 to DP9 XGOS, as produced with the method of the present invention, for producing food products. The invention further provides a food product comprising the XGOS mixture as produced with the method of the invention.

In a further embodiment, the invention provides the XGOS mixture as produced with the method of the invention for use in nutrition, such as for reducing calories in food or to improve the texture of food.

In a further embodiment, the invention provides the XGOS mixture as produced with the method of the invention for human health benefits such as for lowering the blood glucose level after meal intake or as satiety agent. Also contemplated is the use of the XGOS mixture as produced with the method of the invention in methods of treating diseases, such as in a method of treatment of diabetes mellitus, said method comprising the administering of the XGOS mixture as produced with the method of the invention to a subject in need thereof. Further contemplated is the use of the XGOS mixture as produced with the method of the invention for the preparation of a medicament for the treatment of diseases, such as diabetes mellitus.

The XGOS mixture as produced with the method of the invention is also advantageous in animal nutrition. Accordingly, the invention provides the XGOS mixture as produced with the method of the invention for use in animal nutrition and for producing feed products.

The oligosaccharide can be used as prebiotic in human and/or animal nutrition. Accordingly, the invention provides XGOS mixture as produced with the method of the invention for use as prebiotic, e.g. for use in the stimulation of the intestinal microbiota.

The term "prebiotic" is to be understood as a non-digestible, selectively fermented food component which causes specific changes to the composition and/or activity of the intestinal microbiota, beneficial to the health and well-being of the host (Gibson et al., 2004). The prebiotic can in particular be considered as an aliment for favorable bacteria of the colon, such as the bifidobacteria and the lactobacilli, which enable preventing intestinal disorders, enhancing the absorption of minerals, modulating the lipid metabolism, and/or stimulating the immune system.

Since it has been discovered that it was possible to modulate the balance of the intestinal microbiota by ingesting food ingredients, numerous candidates to the appellation "prebiotic" have been studied. Most are carbohydrates of vegetable origin. The most known and the better characterized are the fructans, fructose polymers, among which is inulin, generally extracted from chicory tubers, but also from agave, and the fructo-oligosaccharides (FOS) produced either by hydrolysis of inulin, or by biosynthesis from saccharose—derived fructose.

Other oligosaccharides also have prebiotic properties that are more or less established: the galacto-oligosaccharides (GOS) or "trans-galacto-oligosaccharides" (TOS), very close to the compounds present in mother's milk, the soy oligosaccharides (SOS), the isomalto-oligosaccharides (IMOS), the lactulose, the raffinose, the xylo-oligosaccharides (XOS), etc..

In spite of the numerous studies carried out on the already well characterized prebiotics (such as the FOS and the GOS) as well as on a great number of candidate molecules, there is still, to this day, a lack of a prebiotic combining the following properties which are sought after by the (potential) producers of food and drinks with a health functionality: a simple and economical production method, very good intestinal tolerance allowing for the use of adequate concentrations to obtain, in practice, the desired results, and high stability to heating processes and to the conventional acidic media prevalent in large sectors of the food industry.

The existing prebiotics are used only in a limited number of food applications (humanized milk in particular) and at concentrations which do not always make it possible to guarantee the effects theoretically possible according in vitro/vivo, or even clinical research.

As described herein, the XGOS mixture prepared according to the method of the invention is stable against acid degradation and heat. Moreover, the XGOS mixture prepared according to the method of the invention exhibits in vitro metabolic stability against digestive enzymes. Moreover, there is indication in the scientific literature that xyloglucan derived oligosaccharides are not a common substrate for the intestinal microbiome; but, in contrast said oligosaccharides specifically stimulate *Lactobacillus acidophilus* as well as *Bacteroides ovatus* (Hartemik et al., 1996). Larsbrink et al. 2014, demonstrated that selected human gut bacteria of the genus *Bacteroides* are able to metabolize xyloglucan. Besides prebiotic effects, which are difficult to prove to be beneficial for healthy human, oligosaccharides demonstrated positive effects in respect to digestion and reduction of post-prandial glycaemic responses after food consumption. The EFSA stated that non-digestible carbohydrates including FOS, GOS and other non metabolizable oligosaccharides are resistant to hydrolysis and absorption in the small intestine. The EFSA stated that based on the available evidence on bowel function, the EFFSA panel considers dietary fibre intakes of 25 g/day to be adequate for normal laxation in adults (EFSA Journal 2010; 8(3):1462). In 2014 the EFSA acknowledged health benefits for oligosaccharides containing food/drinks in respect to reduction of post-prandial glycaemic responses and insulinaemic responses compared to sugar-containing foods/drinks. Non-digestible carbohydrates including FOS and GOS do not contribute to post-prandial glycaemia response. This opinion applies to non-digestible carbohydrates (e.g. non-starch polysaccharides, resistant oligosaccharides and resistant starch) which should replace sugars in foods or beverages in order to obtain the claimed effect (EFSA Journal 2014; 12(10):3838 and EFSA Journal 2014; 12(1): 3513).

Other potential uses comprise the isolation and purification of a specific oligosaccharide by chromatography or use of the oligosaccharide mixture as is. The isolated oligosaccharide species could be further derivatized, e.g. by chemical derivatization and used as a structural starting point for the production of compounds, which can be used e.g. as a biosurfactant, an odor-active substance, a structural compound for pharmaceuticals or plastics etc., a surface active substance, a bioactive substance, and others.

Enzymes

The present invention further provides polypeptides, which have the deduced amino acid sequence of SEQ ID NOs 1 to 4, as well as fragments, analogs and derivatives of such polypeptides. The terms "fragment", "derivative" and "analog", when referring to a polypeptide of SEQ ID NOs 1 to 4, means polypeptides that retain essentially the same biological function or activity as a xyloglucanase. An analog might, for example, include a proprotein, which can be activated by cleavage of the proprotein portion to produce an active mature protein. The polypeptides of the present invention may be recombinant polypeptides, natural polypeptides or synthetic polypeptides. The fragment, derivative or analog of a polypeptide of SEQ ID NOs 1 to 4, may be (i) one in which one or more of the amino acid residues is substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which additional amino acids are fused to the mature protein, such as a leader or secretory sequence or a sequence which is employed for purification, or for substrate or complex binding of the mature polypeptide or a proprotein sequence. Such fragments, derivatives and analogs are deemed to be within the scope of those skilled in the art to provide upon the basis of the teachings herein.

The polypeptides of the present invention include the polypeptides of SEQ ID NOs 1 to 4, as well as polypeptides which have at least 75% similarity (e.g. preferably at least 50%; and more preferably at least 70% identity) to a polypeptide of SEQ ID NOs 1 to 4, more preferably at least 85% similarity (e.g. preferably at least 70% identity) to a polypeptide of SEQ ID NOs 1 to 4, and most preferably at least 95% similarity (e.g. preferably at least 90% identity) to a polypeptide of SEQ ID NOs 1 to 4. Moreover, they should preferably include exact portions of such polypeptides containing a sequence of at least 30 amino acids, and more preferably at least 50 amino acids.

Fragments or portions of the polypeptides of the present invention may be employed as intermediates for producing the corresponding full-length polypeptides by peptide synthesis.

Fragments or portions of the polynucleotides of the present invention may also be used to synthesize full-length polynucleotides of the present invention.

In a preferred embodiment, said polypeptide comprises, essentially consists of or consists of a polypeptide which has at least 75% amino acid sequence identity to a polypeptide selected from SEQ ID NO: 1-4 and which shows xyloglucanase, in particular endoglucanase activity.

Such enzymes are especially suitable for use in the processing tamarind polysaccharide according to the method of the invention. The polypeptides provided by the invention still display a sufficient endoglucanase activity to hydrolyze tamarind polysaccharide at high temperatures, i.e. at temperatures above 50° C.

The method and the polypeptides of the present invention are advantageous in that they lead in the production of a hydrolysate, which comprise, essentially consists of or consists of DP7-DP9 XGOS without significant amounts of side products such as other XGOS or monosaccharides.

The invention further relates to a nucleic acid molecule comprising a nucleic acid sequence encoding the polypeptide according to the invention, in particular encoding an amino acid sequence selected from SEQ ID NOs 1 to 4. In a preferred embodiment, the nucleic acid molecule encoding the polypeptide according to the invention is a nucleic acid molecule comprising, essentially consisting of or consisting of the sequence of one of SEQ ID NOs: 11 to 14.

The "polynucleotides" or "nucleic acids" of the present invention may be in the form of RNA or in the form of DNA; DNA should be understood to include cDNA, genomic DNA, recombinant DNA and synthetic DNA. The DNA may be double-stranded or single-stranded and, if single stranded, may be the coding strand or non-coding (antisense) strand. The coding sequence, which encodes the polypeptide may be identical to the coding sequence for the polypeptides shown in SEQ ID NOs: 1 to 4, or it may be a different coding sequence encoding the same polypeptide, as a result of the redundancy or degeneracy of the genetic code or a single nucleotide polymorphism. For example, it may also be an RNA transcript which includes the entire length of the coding sequence for a polypeptide of any one of SEQ ID NOs 1 to 4.

The nucleic acids which encode the polypeptides of SEQ ID NOs: 1 to 4 may include but are not limited to the coding sequence for the polypeptide alone; the coding sequence for the polypeptide plus additional coding sequence, such as a leader or secretory sequence or a proprotein sequence; and the coding sequence for the polypeptide (and optionally additional coding sequence) plus non-coding sequence, such as introns or a non-coding sequence 5' and/or 3' of the coding sequence for the polypeptide.

Thus, the term "polynucleotide encoding a polypeptide" or the term "nucleic acid encoding a polypeptide" should be understood to encompass a polynucleotide or nucleic acid which includes only a coding sequence for a enzyme of the invention, e.g. a polypeptide selected from SEQ ID NOs: 1 to 4 as well as one which includes additional coding and/or non-coding sequence. The terms polynucleotides and nucleic acid are used interchangeably.

The present invention also includes polynucleotides where the coding sequence for the polypeptide may be fused in the same reading frame to a polynucleotide sequence which aids in expression and secretion of a polypeptide from a host cell; for example, a leader sequence which functions as a secretory sequence for controlling transport of a polypeptide from the cell may be so fused. The polypeptide having such a leader sequence is termed a preprotein or a preproprotein and may have the leader sequence cleaved by the host cell to form the mature form of the protein. These polynucleotides may have a 5' extended region so that it encodes a proprotein, which is the mature protein plus additional amino acid residues at the N-terminus. The expression product having such a prosequence is termed a proprotein, which is an inactive form of the mature protein; however, once the prosequence is cleaved an active mature protein remains. The additional sequence may also be attached to the protein and be part of the mature protein. Thus, for example, the polynucleotides of the present invention may encode polypeptides, or proteins having a prosequence, or proteins having both a prosequence and a presequence (leader sequence).

The polynucleotides of the present invention may also have the coding sequence fused in frame to a marker sequence which allows for purification of the polypeptides of the present invention. The marker sequence may be an affinity tag or an epitope tag such as a polyhistidine tag, a streptavidin tag, a Xpress tag, a FLAG tag, a cellulose or chitin binding tag, a glutathione-S transferase tag (GST), a hemagglutinin (HA) tag, a c-myc tag or a V5 tag.

The HA tag would correspond to an epitope derived from the influenza hemagglutinin protein (Wilson, I., et al., Cell, 37: 767 (1984)), and the c-myc tag may be an epitope from human Myc protein (Evans, G. I. et al., Mol. Cell. Biol. 5: 3610-3616 (1985)).

The present invention is considered to further provide polynucleotides which hybridize to the hereinabove-described sequences wherein there is at least 70%, preferably at least 90%, and more preferably at least 95% identity or similarity between the sequences, and thus encode proteins having similar biological activity. Moreover, as known in the art, there is "similarity" between two polypeptides when the amino acid sequences contain the same or conserved amino acid substitutes for each individual residue in the sequence. Identity and similarity may be measured using sequence analysis software (e.g., ClustalW at PBIL (Pole Bioinformatique Lyonnais) http://npsa-pbil.ibcp.fr). The present invention particularly provides such polynucleotides, which hybridize under stringent conditions to the hereinabove-described polynucleotides.

Suitably stringent conditions can be defined by, e.g., the concentrations of salt or formamide in the prehybridization and hybridization solutions, or by the hybridization temperature, and are well known in the art. In particular, stringency can be increased by reducing the concentration of salt, by increasing the concentration of formamide, and/or by raising the hybridization temperature.

For example, hybridization under high stringency conditions may employ about 50 formamide at about 37° C. to 42° C., whereas hybridization under reduced stringency conditions might employ about 35% to 25% formamide at about 30° C. to 35° C. One particular set of conditions for hybridization under high stringency conditions employs 42° C., 50% formamide, 5×SSPE, 0.3% SDS, and 200 μg/mL sheared and denatured salmon sperm DNA. For hybridization under reduced stringency, similar conditions as described above may be used in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art. Preferably, hybridization should occur only if there is at least 95%, and more preferably at least 97%, identity between the sequences. The polynucleotides which hybridize to the hereinabove described polynucleotides in a preferred embodiment encode polypeptides which exhibit substantially the same biological function or activity as the protein of SEQ ID NOs: 1 to 4.

As mentioned, a suitable polynucleotide probe may have at least 14 bases, preferably 30 bases, and more preferably at least 50 bases, and will hybridize to a polynucleotide of the present invention, which has an identity thereto, as hereinabove described, and which may or may not retain activity. For example, such polynucleotides may be employed as a probe for hybridizing to the polynucleotides encoding the polypeptides of SEQ ID NOs: 1 to 4, respectively, for example, for recovery of such a polynucleotide, or as a diagnostic probe, or as a PCR primer. Thus, the present invention includes polynucleotides having at least a 70 identity, preferably at least a 90% identity, and more preferably at least a 95% identity to a polynucleotide which encodes a polypeptide of SEQ ID NOs 1 to 4, as well as fragments thereof, which fragments preferably have at least 30 bases and more preferably at least 50 bases, and to polypeptides encoded by such polynucleotides.

The terms "homology" or "identity," as used interchangeably herein, refer to sequence similarity between two polynucleotide sequences or between two polypeptide sequences, with identity being a more strict comparison. The phrases "percent identity or homology" and "identity or homology" refer to the percentage of sequence similarity found in a comparison of two or more polynucleotide sequences or two or more polypeptide sequences. "Sequence similarity" refers to the percent similarity in base pair sequence (as determined by any suitable method) between two or more polynucleotide sequences. Two or more sequences can be anywhere from 0-100% similar, or any integer value there between. Identity or similarity can be determined by comparing a position in each sequence that can be aligned for purposes of comparison. When a position in the compared sequence is occupied by the same nucleotide base or amino acid, then the molecules are identical at that position. A degree of similarity or identity between polynucleotide sequences is a function of the number of identical or matching nucleotides at positions shared by the polynucleotide sequences.

A degree of identity of polypeptide sequences is a function of the number of identical amino acids at positions shared by the polypeptide sequences. A degree of homology or similarity of polypeptide sequences is a function of the number of amino acids at positions shared by the polypeptide sequences. The term "substantially identical," as used herein, refers to an identity or homology of at least 70%, 75%, at least 80%, at least 85%, at least 90%, 91%, 92%, 93%, 94%, 95%, 96%, 97%, 98%, 99%, or more.

The degree of sequence identity is determined by choosing one sequence as the query sequence and aligning it with the internet-based tool ClustalW with homologous sequences taken from Gen Bank using the blastp algorithm (NCBI).

As is well known in the art, the genetic code is redundant in that certain amino acids are coded for by more than one nucleotide triplet (codon), and the invention includes those polynucleotide sequences which encode the same amino acids using a different codon from that specifically exemplified in the sequences herein. Such a polynucleotide sequence is referred to herein as an "equivalent" polynucleotide sequence. The present invention further includes variants of the hereinabove described polynucleotides which encode for fragments, such as part or all of the protein, analogs and derivatives of a polypeptide of SEQ ID NOs 1 to 4. The variant forms of the polynucleotide may be a naturally occurring allelic variant of the polynucleotide or a non-naturally occurring variant of the polynucleotide. For example, the variant in the nucleic acid may simply be a difference in codon sequence for the amino acid resulting from the degeneracy of the genetic code, or there may be deletion variants, substitution variants and addition or insertion variants. As known in the art, an allelic variant is an alternative form of a polynucleotide sequence, which may have a substitution, deletion or addition of one or more nucleotides that does not substantially alter the biological function of the encoded polypeptide.

The present invention also includes vectors, which include such polynucleotides, host cells which are genetically engineered with such vectors and the production of the polypeptides of SEQ ID NOs: 1 to 4 by recombinant techniques using the foregoing. Host cells are genetically engineered (transduced or transformed or transfected) with such vectors, which may be, for example, a cloning vector or an expression vector. The vector may be, for example, in the form of a plasmid, a conjugative plasmid, a viral particle, a phage, etc. The vector or the gene may be integrated into the chromosome at a specific or a not specified site. Methods for genome integration of recombinant DNA, such as homologous recombination or transposase-mediated integration, are well known in the art. The engineered host cells can be cultured in conventional nutrient media modified as appropriate for activating promoters, selecting transformants or amplifying the genes of the present invention. The culture conditions, such as temperature, pH and the like, are those commonly used with the host cell selected for expression, as well known to the ordinarily skilled artisan.

The polynucleotides of the present invention may be employed for producing the polypeptides of SEQ ID NOs: 1 to 4 by recombinant techniques. Thus, for example, the polynucleotides may be included in any one of a variety of expression vectors.

The appropriate DNA sequence may be inserted into the vector by any of a variety of procedures. In general, the DNA sequence is inserted into an appropriate restriction endonuclease site(s) by procedures well known in the art, which procedures are deemed to be within the scope of those skilled in this art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli lac, ara, rha or trp, the phage lambda P. sub.L promoter and other promoters known to control expression of genes in prokaryotic or eukaryotic cells or their viruses.

More preferably, the polypeptides of the invention can be expressed using the following tools:

Specific examples of suitable promoters for directing the transcription of the nucleic acid constructs of the present invention, especially in a bacterial host cell, are the promoters obtained from the E. coli lac operon, Streptomyces coelicolor agarase gene (dagA), Bacillus subtilis levansucrase gene (sacB), Bacillus licheniformis alpha-amylase gene (amyL), Bacillus stearothermophilus maltogenic amylase gene (amyM), Bacillus amyloliquefaciens alpha-amylase gene (amyQ), Bacillus licheniformis penicillinase gene (penP), Bacillus subtilis xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in Scientific American, 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from the gene encoding neutral alpha-amylase in *Aspergillus niger* in which the untranslated leader has been replaced by an untranslated leader from the gene encoding triose phosphate isomerase in *Aspergillus nidulans*); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, Yeast 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator that is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a non-translated region of an mRNA that is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and, when transcribed, is recognized by the host cell as a signal to add polyadenosine residues to transcribed mRNA. Any polyadenylation sequence that is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding sequence that encodes a signal peptide linked to the amino terminus of a polypeptide and directs the encoded polypeptide into the cell's secretory pathway. The 5' end of the coding sequence of the nucleotide sequence may inherently contain a signal peptide coding sequence naturally linked in translation reading frame with the segment of the coding sequence that encodes the secreted polypeptide.

Alternatively, the 5' end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice, i.e., secreted into a culture medium, may be used in the present invention.

Effective signal peptide coding sequences for bacterial host cells are the signal peptide coding sequences obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva 1993 and by Brockmeier et al., 2006.

Effective signal peptide coding sequences for filamentous fungal host cells are the signal peptide coding sequences obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the amino terminus of a polypeptide. The resultant polypeptide is known as a proenzyme or propolypeptide (or a zymogen in some cases). A propeptide is generally inactive and can be converted to a mature active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide sequences are present at the amino terminus of a polypeptide, the propeptide sequence is positioned next to the amino terminus of a polypeptide and the signal peptide sequence is positioned next to the amino terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus nigerglucoamylase* promoter, and *Aspergillus oryzae* glucoamylase promoter may be used as regulatory sequences. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described herein may be joined together to produce a recombinant expression vector that may include one or more (several) convenient restriction sites to allow for insertion or substitution of the nucleotide sequence encoding the polypeptide at such sites. Alternatively, a polynucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vectors of the present invention preferably contain one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like (Kroll et al. 2009-Establishment of a novel anabolism-based addiction system with an artificially introduced mevalonate pathway: Complete stabilization of plasmids as universal application in white biotechnology). These auxotrophies include but are not limited to disruptions or deletions in amino acid biosynthesis for alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine, respectively. The auxotrophic phenotype is complemented episomal together with an expression cassette of the gene of interest.

Examples of bacterial selectable markers are the dal genes from *Bacillus subtilis* or *Bacillus licheniformis*, or markers that confer antibiotic resistance such as ampicillin, kanamycin, chloramphenicol, or tetracycline resistance. Suitable markers for yeast host cells are ADE2, HIS3, LEU2, LYS2, METS, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), meta (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cells are the 2 micron origins of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, Gene 98: 61-67; Cullen et al., 1987, Nucleic Acids Research 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

In a preferred embodiment, the invention provides a host cell expressing the polypeptide according to one of SEQ ID NOs: 1 to 4. More preferably, said host cell of comprises the nucleotide molecule of the invention, which encodes for a polypeptide of SEQ ID NOs: 1 to 4. Most preferably, said host cell is *E. coli* or *Bacillus subtilis*.

The present invention provides in a further embodiment a method for producing the polypeptide of SEQ ID NOs: 1 to 4, the method comprising culturing a host cell as described herein under conditions permitting the production of the enzyme, and recovering the enzyme from the culture.

Methods of Production

More preferably, the present invention provides methods of producing a polypeptide of the present invention, i.e. a polypeptide of SEQ ID NOs: 1 to 4, comprising: (a) cultivating a cell, which produces the polypeptide, under conditions conducive for production of the polypeptide; and (b) recovering the polypeptide. In a preferred aspect, the cell is of the genus *Bacillus*. In a more preferred aspect, the cell is *Bacillus subtilis* or *Bacillus licheniformis*.

The present invention also relates to methods of producing a polypeptide of the present invention, comprising: (a) cultivating a recombinant host cell, as described herein, under conditions conducive for production of the polypeptide; and (b) recovering the polypeptide.

In the production methods of the present invention, the cells are cultivated in a nutrient medium suitable for production of the polypeptide using methods well known in the art. For example, the cell may be cultivated by shake flask cultivation, or small-scale or large-scale fermentation (including continuous, batch, fed-batch, or solid-state fermentations) in laboratory or industrial fermenters performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g. in catalogues of the American Type Culture Collection). If the polypeptide is secreted into the nutrient medium, the polypeptide can be recovered directly from the medium. If the polypeptide is not secreted into the medium, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989) to obtain substantially pure polypeptides.

Compositions

The present invention also relates to compositions comprising a polypeptide of the present invention, i.e. a polypeptide of SEQ ID NOs: 1 to 4. Preferably, the compositions are enriched in such a polypeptide. The term "enriched" indicates that the endoglucanase activity of the composition has been increased, e.g., with an enrichment factor of at least 1.1.

The polypeptide compositions may be prepared in accordance with methods known in the art and may be in the form of a liquid or a dry composition. The polypeptide to be included in the composition may be stabilized in accordance with methods known in the art and as described hereinbefore.

Enzyme Preparation

The invention further provides an enzyme preparation comprising a polypeptide of SEQ ID NOs: 1 to 4, for use in hydrolysis of xyloglucan polysaccharide in the process of the invention. The enzyme preparation is preferably in the form of a liquid, granulate or agglomerated powder, more preferably in the form of a granulate or agglomerated powder.

The granulate or agglomerated powder has preferably a narrow particle size distribution with more than 95% (by weight) of the particles in the range from 25 to 500 μm.

Granulates and agglomerated powders may be prepared by conventional methods, e.g. by spraying the enzyme onto a carrier in a fluid-bed granulator. The carrier may consist of particulate cores having a suitable particle size. The carrier may be soluble or insoluble, e.g. a salt (such as sodium chloride or sodium sulfate), a sugar (such as sucrose or lactose), a sugar alcohol (such as sorbitol), starch, rice, corn grits, or soy.

The present invention is further described by the following figures and examples that should not be construed as limiting the scope of the invention.

Herein,

FIG. 1 shows the hydrolysis of tamarind xyloglucan to oligosaccharides DP7 to DP9. Possible sites for hydrolysis by an endoglucanase are indicated by a scissors symbol. In XXXG, XXLG, XLXG and XLLG describes the structure of the oligosaccharides, with G designating an undecorated backbone glucose residue, X a backbone glucose residue decorated with xylose, and L a backbone glucose residue decorated with xylose and galactose; letter code naming convention from Fry et al, 1993.

Figure 6:
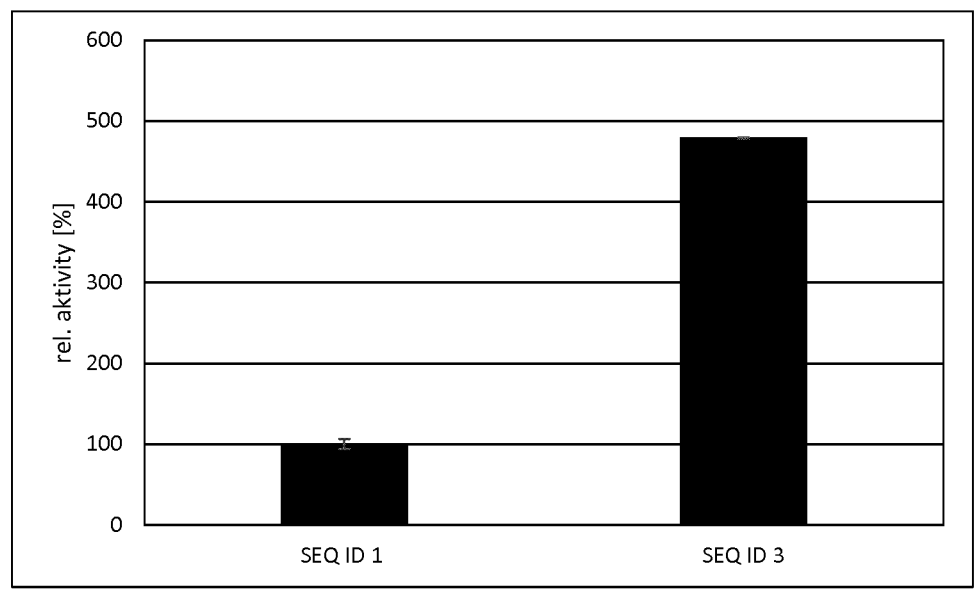

FIG. 6 shows the relative enzyme activity of SEQ ID NOs 1 and 3 respectively. The enzyme activity of SEQ ID NO 1 was set to 100%. Surprisingly, the SEQ ID NO 3 enzyme activity increases >4 fold in comparison to SEQ ID NO 1 enzyme activity.

Enzyme activity: the release of micromol reducing sugars from arabinoxylan per mg of enzyme was determined with the DNSA assay.

Figure 7:
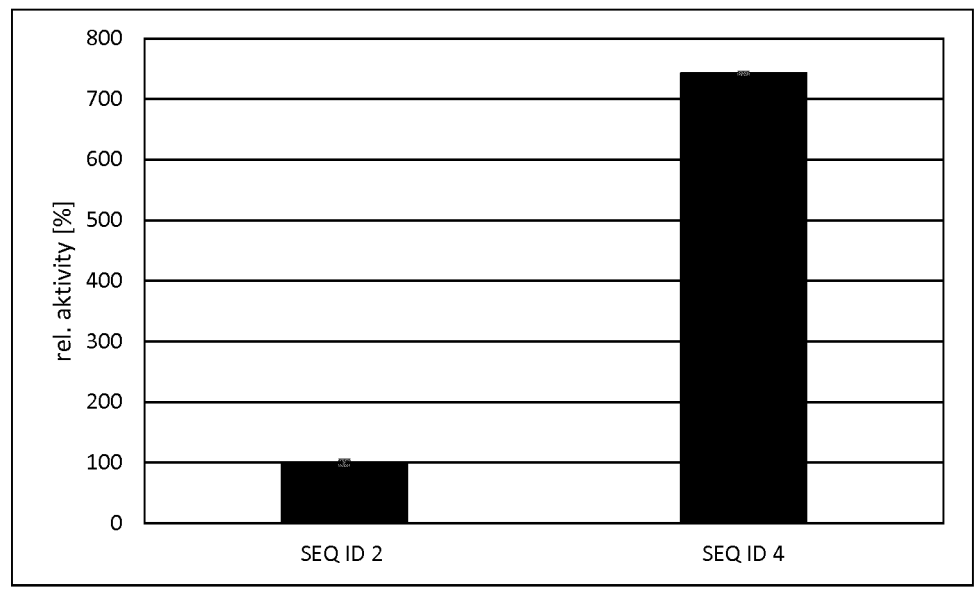

FIG. 7 shows the relative enzyme activity of SEQ ID NOs 2 and 4 respectively. The enzyme activity of SEQ ID NO 2 was set to 100%. Surprisingly, the SEQ ID NO 4 enzyme activity increases >7 fold in comparison to SEQ ID NO 1 enzyme activity.

Enzyme activity: the release of micromol reducing sugars from arabinoxylan per mg of enzyme was determined with the DNSA assay.

Figure 8:
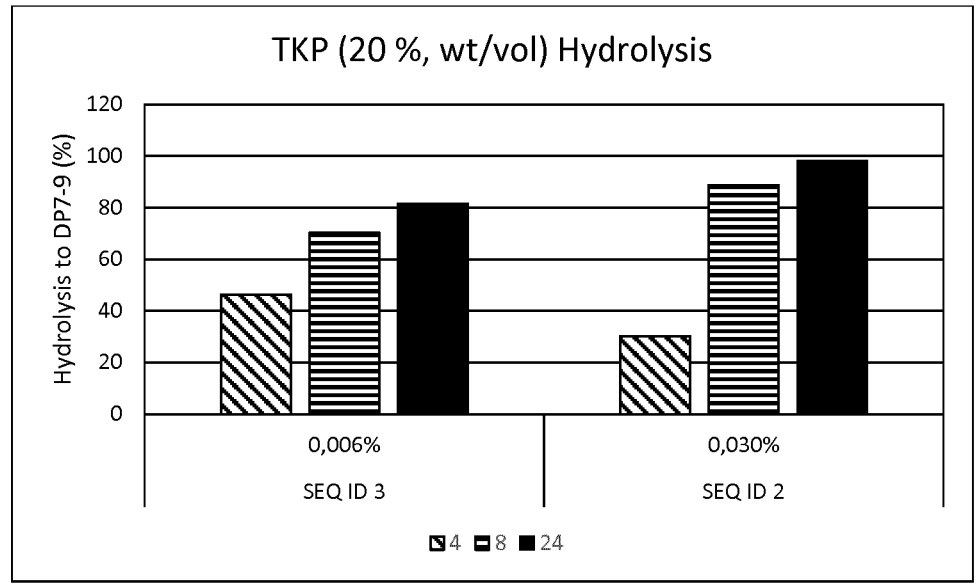

FIG. 8 shows the XGOS release from 20% (wt/vol) dTKP by 0.006% (wt/wt) SEQ ID NO 3 and 0.03% (wt/wt dTKP) enzymes SEQ ID NO 2. The enzyme reactions were performed at 60° C. Complete hydrolysis was achieved after 24 h for SEQ ID NO 2 and over 80% after 24 h for SEQ ID NO 3.

Figure 9:
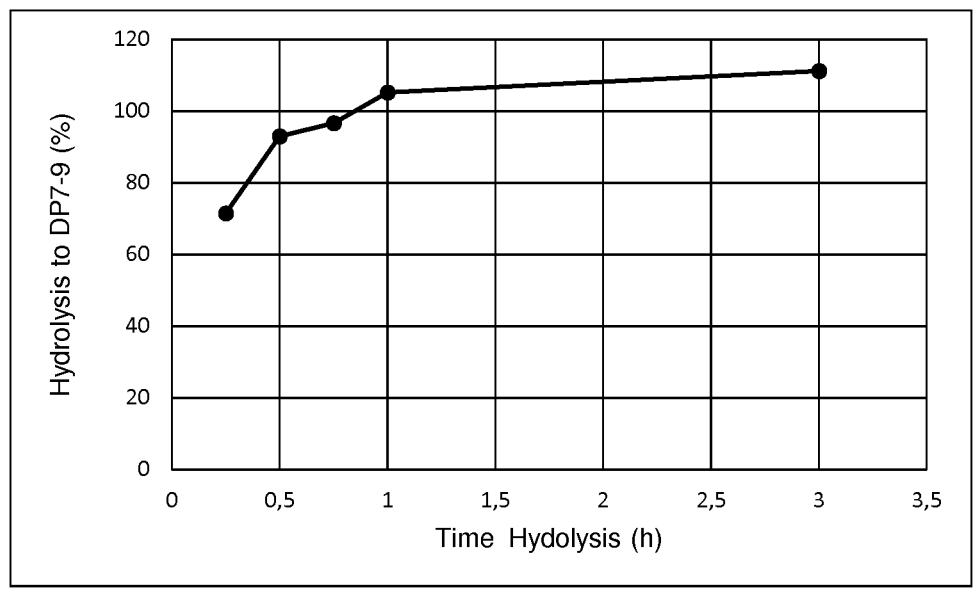

FIG. 9 shows the XGOS release from dTKP by 0.65% (wt/wt dTKP) SEQ ID NO 3 and 20% TKP substrate. The enzyme reaction was performed at 60° C. The dTKP contains 65% (wt/wt) xyloglucan which is completely degraded to XGOS DP7-9 by SEQ ID NO 3 within 1 h.

Figure 10:
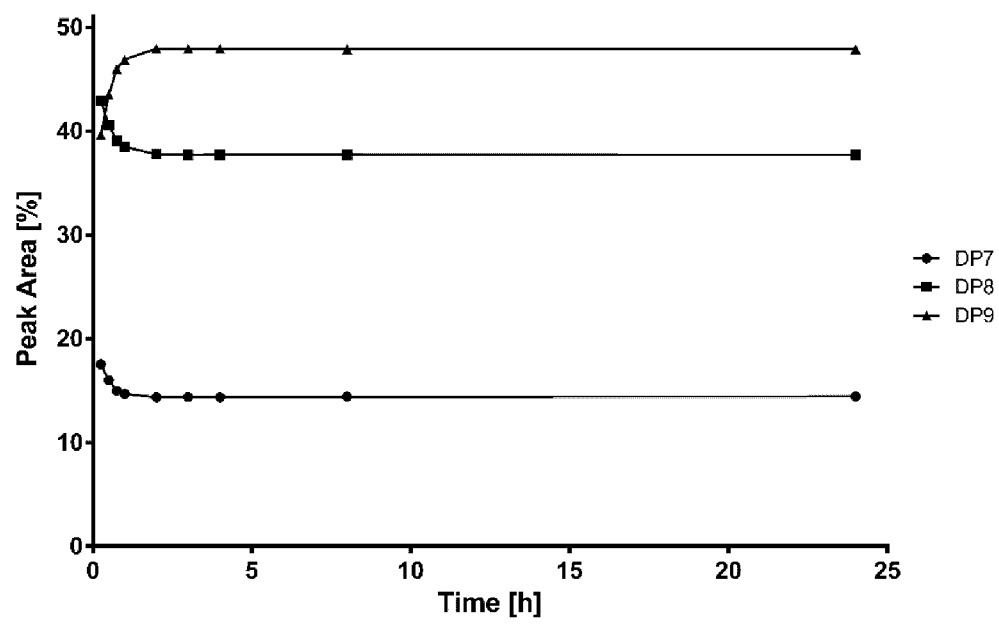

FIG. 10 shows the hydrolysis stability of the XGOS mixture produced with the method of the invention: TKP 20% (wt/vol) hydrolysis, 0-24 h at 60° C. with 3% (wt/wt dTPK) SEQ ID NO 3 and subsequent HPAEC-PAD analytic. The HPAEC results were subsequently converted to oligosaccharide ratios (DP7-DP9) over time.

Figure 11:
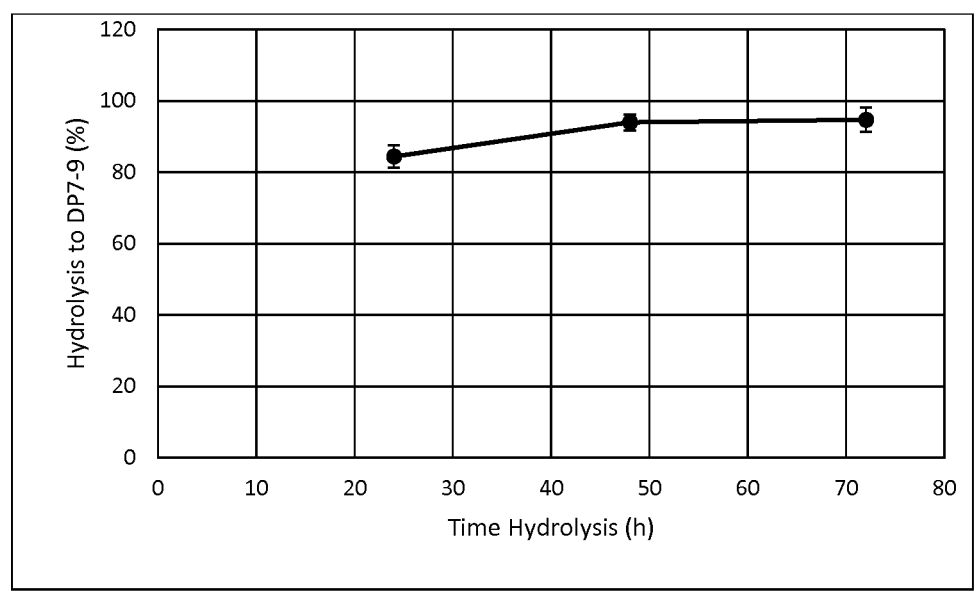

FIG. 11 shows TKP hydrolysis of high substrate concentration (up to 700 g/L) with the method of the invention: 0-72 h with 0.05% SEQ ID NO 3. Degree of hydrolysis was confirmed by HPAEC-PAD analytic.

EXAMPLES

Example 1: Cloning of SEQ ID NOs 11-14 Encoding Endoglucanases and Expression of SEQ ID NOs 1-4

All Chemicals used as buffers and substrates were commercial products of at least reagent grade.

Cloning of SEQ ID NO 2: A new cellulose degrading bacterial strain named *Herbivorax saccincola* DSM101079 was isolated from a 20 l fermenter operated with cow manure and fed with maize silage at 55° C. *Herbivorax saccincola* was classified as a new family in the Ruminococcaceae (Koeck et al. 2016). For genome sequencing of the strain *Herbivorax saccincola* DSM101079, a total of 4 μg genomic DNA was used to construct an 8-k mate-pair sequencing library (Nextera Mate Pair Sample Preparation Kit, Illumina Inc.), which was sequenced applying the paired-end protocol on an Illumina MiSeq system. Analysis and interpretation of the *Herbivorax saccincola* DSM101079 genome sequence within GenDB and by means of the Carbohydrate-active-enzyme database dbCAN (Yin et al., 2012) revealed more than 100 genes predicted to encode enzymes that mainly belong to different families of Glycoside Hydrolases (GH) and Carbohydrate-Binding Modules (CBM). SEQ ID NO 2 was identified as coding sequence for a glycoside hydrolase family 5 member.

The genes SEQ ID NOs 11 and 12 encoding endoglucanases were produced by recombinant *E. coli* strains. DNA was amplified using PCR with primers SEQ ID NOs 5-10 and cloned into NdeI/XhoI-linearized pET24c(+) Vector (Novagen, MerckMillipore) under control of the inducible T7-promoter using Gibson Assembly (NEB, Cat. Nr. E2611S). For SEQ ID NO 11 oligonucleotide primers (SEQ ID NO 5) and (SEQ ID NO 7) were used. Variant SEQ ID NO 13, a shortened variant of SEQ ID NO 11, was amplified using oligonucleotide primers (SEQ ID NO 5) and (SEQ ID NO 6). For SEQ ID NO 12 DNA amplification the oligonucleotide primers (SEQ ID NO 8) and (SEQ ID NO 9) were used. Variant SEQ ID NO 14, a shortened variant of SEQ ID NO 12, was amplified using the oligonucleotide primers (SEQ ID NO 8) and (SEQ ID NO 10). Chemically competent E. coli DH10B (Invitrogen, Fisher Scientific, Schwerte, Germany) were transformed. Positive clones were selected by colony PCR using primer combination as described above. For SEQ ID NOs 1-4 protein expression chemically competent E. coli BL21 Star (DE3) (Invitrogen, Fisher Scientific, Schwerte, Germany) were transformed with the respective expression vector.

Growth of Cells

Fed-batch fermentations of recombinant E. coli strains harbouring the endoglucanase genes from C. thermocellum ATCC27405/DSM1237 of SEQ ID NOs 1 and 3, and Herbivorax saccincola DSM101079 gene SEQ ID NO 2 and 4 were carried out in a 10 L Uni-Vessel controlled and equipped with a Biostat B Twin DCU (Sartorius A G, Gottingen, Germany). Temperature, pH, foam, turbidity, weight and dissolved oxygen were monitored online during fermentation. The dissolved oxygen (DO %) was set to 25% (vol/vol) and maintained with increasing agitation and constant air flow. The formation of foam was controlled by the addition of Antifoam 206 (Sigma Aldrich, St. Louis, Mo., USA). A pH of 6.9 was maintained by addition of a 25% (vol/vol) ammonium hydroxide solution and 25% (vol/vol) $HPO_4$ solution. E. coli strains were cultivated in Riesenberg medium (Korz et al., 1995) at the 10 L scale, the feeding solution consists of 1021 g/L glycerol, 20 g/L $MgSO_4.7H_2O$, 13 mg/L EDTA, 4 mg/L $CoCl_2.6H_2O$, 23.5 mg/L $MnCl_2.4H_2O$, 2.5 mg/L $CuCl_2.2H_2O$, 5 mg/L $H_3BO_3$, 4 mg/L $Na_2MoO_4 \times 2\ H_2O$, 16 mg/L $Zn(CH_3C00)_2.2H_2O$, 40 mg/L Fe(III)citrate (Korz et al., 1995).

After the consumption of the initial carbohydrate substrate, growth rate was controlled according to EQUATION 1, whereby ms, is the mass flow of substrate (g h$^{-1}$), $\mu_{set}$ the desired specific growth rate (h$^{-1}$), $Y_{X/S}$ the biomass/substrate yield coefficient (g g$^{-1}$), m the specific maintenance coefficient (g g$^{-1}$ h$^{-1}$), V the cultivation volume (L), and X the biomass concentration (g L$^{-1}$):

$$m_S = \left(\frac{\mu_{set}}{Y_{X/S}} + m\right) \cdot V(t) \cdot X(t) \cdot e^{\mu_{set}(t-t_F)} \quad \text{EQUATION 1}$$

The inoculation procedure was the following: Based on a cryo-stock, a fresh agar plate containing adequate antibiotics was prepared. With one colony an Erlenmeyer flask containing 30 mL Lysogeny Broth (Sambrook et al. 1989) was inoculated and incubated for 12 to 15 h at 30° C. 30 mL of this first preculture was used to inoculate 500 mL of the fermentation medium in a 5 L Erlenmeyer flask and incubated for further 14 h. The 10 L fermenter was filled with 6 L fermentation medium and inoculated with 500 mL of the second preculture. Kanamycin was added at 50 μg/mL. Protein production was induced by changing the glycerol feed to lactose feed. Cells were harvested after 48 h by centrifugation for 1 h at 9000 rpm and 22° C. Portions of 300 g cells were solved in 3 L lysis buffer (50 mM MOPS pH 7.3, 0.1 M NaCl, 20 mM imidazol). Cell lysis was achieved by ultrasonic treatment in a ultrasonic flow through chamber. Cell debris was separated by centrifugation (9000 rpm, 22° C.). Supernatant was clarified from residual cells or debris by tangential filtration applying a 0.2 μm filter cassette and three volumes washing with lysis buffer. The enzyme solution was concentrated employing tangential filtration with a 30 kDa filter cassette followed by dialysis with three volumes lysis buffer. GH10 xylanases were purified by immobilized metal ion affinity chromatography (IMAC). Pure enzymes were eluted with elution buffer containing 50 mM MOPS, pH 7.3, 0.25 M imidazole, 0.1 M NaCl, and 20 mM $CaCl_2$).

Protein expression was monitored by SDS-PAGE using 12.5% gels (Bio-Rad Laboratories GmbH, Muenchen) and Coomassie blue staining. Proteins were resuspended in denaturating buffer and heated for 15 min at 95° C. The PageRuler Prestained Protein Ladder 10 to 180 kDa (#26616, ThermoFisher Scientific) was used as molecular weight standard. The proteins were stained with Coomassie brilliant blue R-250 (Weber and Osbourne 1969). Sodium dodecyl sulphate (SDS) polyacrylamide gel electrophoresis was performed according to Laemmli (1970). The protein amount was determined by using Pierce™ BCA Protein Assay Kit (#23225, ThermoFisher Scientific).

Another possibility producing the endoglucanases SEQ ID NOs 1-4 of the invention is to transform a competent B. subtilis strain with an appropriate vector containing the DNA and cultivate the recombinant strain according to Park et al. 1991.

Example 2: Characterization of SEQ ID NOs 1-4

Specific enzyme activity was determined by using a model substrate such as barley-beta-glucan (Megazyme). Endoglucanase activity is defined as the generation of reducing sugars from the model substrate. One unit of enzyme activity is defined as the amount of reducing sugars in micromol generated per mg of enzyme in one minute at 60° C. To define the enzyme profile and temperature and pH optimum the endoglucanases (50 ng/reaction) were incubated for 30 minutes at a temperature range from 50 to 80° C. in presence of 1% (wt/vol) barley-beta-glucan solved in citrate buffer with varying pH (range 4.0-8.0) (solution A: 0.2 M citric acid, 0.1 M NaCl; solution B: 0.4 M $Na_2HPO_4$, 0.1 M NaCl). Reducing sugars were measured by 3,5-dinitrosalicylic acid (DNSA) method: 50 microL sample were mixed with 75 microL DNSA-solution (10 g/L DNSA, 200 g/L K$^+$-Na$^+$-Tartrate, 10 g/L NaOH, 0.5 g/L $Na_2SO_4$, 2 g/L Phenol) in microtiter plates, incubated for 5 minutes at 95° C., cooled on ice and the absorption determined at 540 nm. For calibration, glucose solutions between 0 and 2 mg/mL were used.

Figure 4:
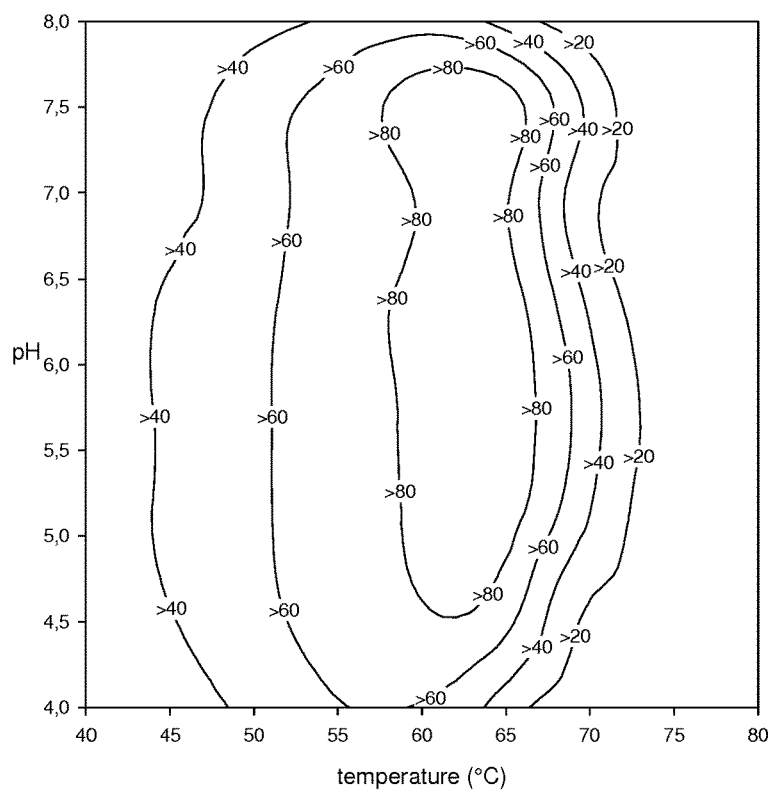
FIG. 4 shows the activity profile of the employed endoglucanase SEQ ID NO 3 in dependence of pH and temperature. Relative activity was determined as generation of reduced sugars from barley-beta-glucan determined by DNSA-assay.
Figure 5:
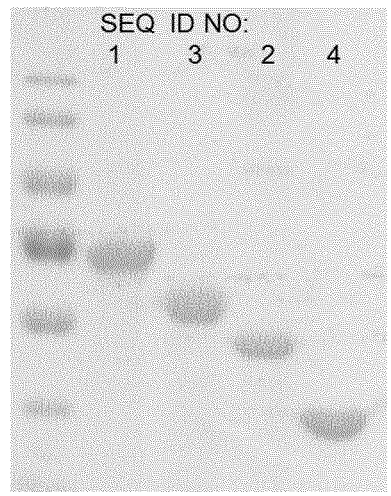
FIG. 5 shows a SDS-PAGE of recombinantly produced SEQ ID NOs 1, 2, 3 and 4 respectively. PageRuler Prestained Protein Ladder 10 to 18 kDa (#26616, ThermoFisher Scientific) was used as protein standard.

The temperature and pH profile of SEQ ID NOs 1-4 showed optimum temperatures at about 60° C., pH 5.5-7.5. As one representative enzyme the SEQ ID NO 3 enzyme activity profile is shown in FIG. 4 and demonstrates a broad temperature profile above 50° C. The other SEQ ID NOs 1, 2 and 4 show a similar enzyme profile. As described in example 2 the SEQ ID NOs 11 and 12 represents the wildtype genes. SEQ ID NOs 13 and 14 are variants of SEQ ID NOs 11 and 12 respectively, lacking the dockerin modules thereby reducing the overall protein size by approximately 15% (FIG. 5). Surprisingly compared to the wildtype protein SEQ ID NOs 1 and 2, the specific enzyme activities of SEQ ID NOs 3 and 4 are at least 4,5 fold increased (FIGS. 6 and 7). The activity increase cannot be explained by the size reduction only. All enzymes SEQ ID NOs: 1-4 are characterized by an enzyme activity suitable to hydrolyze TKP at temperatures above 50° C. equally well as shown for SEQ ID NOs 2 and 3 in FIG. 8.

To evaluate the suitability of SEQ ID NOs 1-4 for TKP hydrolysis, the Ki value of SEQ ID NO 3 was determined. Enzymatic activity was measured on Azo-Xyloglucan (Megazyme) according to the manufacturer's instruction. Substrate concentrations of 1-20 g/l were chosen and enzymatic activity was measured in the presence of increasing concentrations of xyloglucan oligosaccharides. Mode of Inhibition was assessed using a Lineweaver-Burke plot. Nonlinear regression fit of experimental data for SEQ ID NO 3 with GraphPad Prism6 using non-competitive inhibition model gave a $K_i$ value of 16.75 mM (±1.35).

Example 3: Hydrolysis of TKP

The tamarind kernel powder (TKP) and deoiled tamarind kernel powder (dTKP) were purchased from Tamarind Magic, Hyderabad, Phase-IV, 3rd Gate, IDA, Cherlapally, Hyderabad—500051, Telangana, India. Both, TKP and dTKP consist of approximately 65% (wt/wt) xyloglucan (https://www.altrafine.com/tamarind-kernel-powder//.

For XGOS release 20% (wt/vol) 8 g of TKP or dTKP was dissolved in 40 ml demineralized water at 60° C. The enzyme was added at the desired concentrations, 3%, 0.65%, 0.05%, 0.03% or 0.006% (wt/wt TKP) referred to the substrate load. Incubation of the reaction mixture was carried out on a rotary shaker at 125 rpm and 60° C. The hydrolysis process was monitored by taking samples at different time points. The samples were centrifuged and the supernatant boiled for 5 min at 95° C. to denature residual proteins. For analysis, samples of the supernatant were withdrawn, tenfold diluted with double deionized water and measured by HPAEC-PAD.

Example 4: Hydrolysis of up to 700 g TKP/l 25 g/L TKP was dissolved in demineralized water at 60° C. The enzyme was added at the desired concentration of 0.05% related to the final substrate load of 700 g/L. The hydrolysis process was carried out in a 2 L stirred tank reactor (Sartorius AG, Gottingen, Germany) equipped with a three segment impeller agitated between 250 and 500 rpm at 60° C. for 72 h. The substrate was fed with a rate of 25 g/l/h until the final substrate load 700 g/l was achieved. For process monitoring, samples were taken from the reactor at different time points. The samples were centrifuged and the supernatant boiled for 5 min at 95° C. to denature residual proteins. XGOS were isolated in 5 mL samples from the supernatant by alcoholic precipitation as described in example 5 and weighted. For analysis, samples of the supernatant were withdrawn diluted with double deionized water and measured by HPAEC-PAD as described in example 7. A hydrolysis degree over 75% was reached after 24 h and was even further enhanced to over 80% by prolonging the reaction time to 72 h.

Example 5: XGOS Purification Including Ethanol Precipitation

Figure 1:
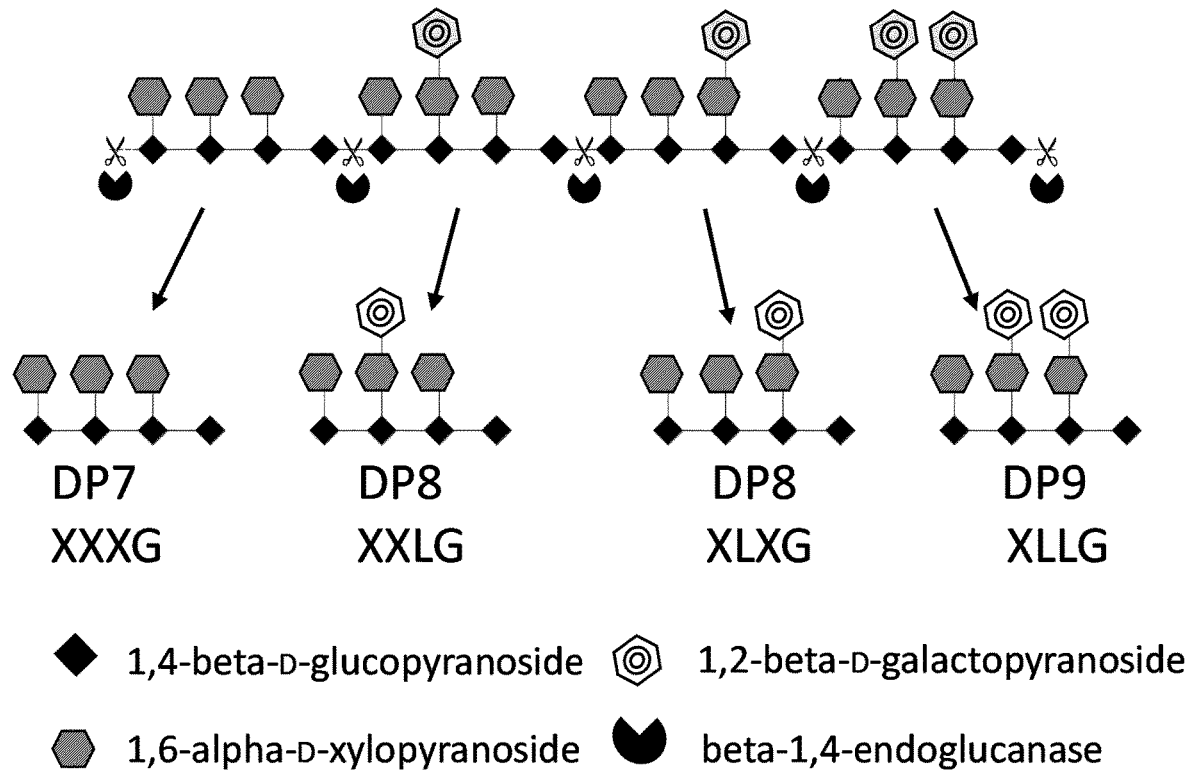
Figure 2:
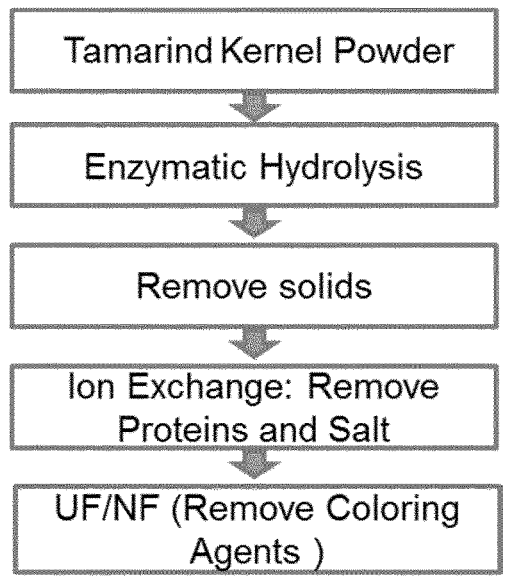
FIG. 2 shows the typical steps of the method of the invention to produce a DP7-DP9 XGOS containing hydrolysate from tamarind kernel powder.
Figure 3:
FIG. 3 shows a photograph of purified DP7-DP9 XGOS mixture in powder form, which was produced with the method of the invention.

To obtain pure XGOS powder (FIG. 3), hydrolysates from example 3 and 4 were separated by centrifugation to separate the insoluble fraction of TKP/dTKP (9,000 rpm, 20 min, RT). One example to further use the insoluble fraction might be as protein enriched, high fat matrix for animal feed. The supernatant is clarified first by microfiltration (tangential filtration, 0.2 micrometer filter cassettes) and second by ultrafiltration (tangential filtration, 10 kDa filter cassettes). Residual proteins, peptides, fatty acids or pigments were removed by ethanol precipitation with ethanol concentrations up to 90% (vol/vol) and incubation on ice for one hour. The precipitate is removed by centrifugation and the supernatant is concentrated and ethanol recycled by rotary evaporation. The precipitate is dried by lyophilisation, desiccator or spray drying.

Example 6: XGOS Purification without Ethanol Precipitation

To obtain pure XGOS powder (FIG. 3), hydrolysates from example 3 were separated by centrifugation to separate the insoluble fraction of TKP/dTKP (9,000 rpm, 20 min, RT). The supernatant is clarified first by microfiltration (tangential filtration, 0.2 microm filter cassettes) and second by ultrafiltration (tangential filtration, 10 kDa filter cassettes). Concentration of DP7-DP9 was achieved by using (sequential) simulated moving bed chromatography or nanofiltration for larger scale. The filtrates or extracts were dried by lyophilisation, desiccator or spray drying.

Example 7: Oligosaccharide Analytics

For the analysis by HPAEC-PAD an ICS 3000 Dionex chromatography system from Thermo Fisher Scientific (Waltham, USA) equipped with a CarboPac™ PA1 column (4×250 mm) and a PA1-precolumn (4×50 mm) was used. The system was set up using PEEK tubing (0.25 mm i.d.), a GM-4 gradient mixer (2 mm), an ED amperometry cell with 0.25 microL channel volume, a pH-Ag/AgCl reference electrode, 0.002" gasket and disposable gold electrodes. Runs were performed at a column temperature of 30° C. with an injection volume of 25 microL and a flow rate of 1 mL/min. The eluent gradient used for the analyte separation started at 0 min with 100 mM NaOH and 7.5 mM sodium acetate (NaOAc). The latter was linearly increased to 100 mM at 67.5 min while 100 mM NaOH was maintained. To wash the column, the concentration of NaOAc was increased to 650 mM with 100 mM NaOH for 4 min and subsequently re-equilibrated with 100 mM NaOH for 16.3 min after each run. The carbohydrate detection with the PAD was based on the waveform "standard carbohydrate quad" (Waveform B) which was set to 2 Hz.

Prior to the analysis of the polysaccharide hydrolysates, the samples were diluted with double-distilled water to a final XGOS concentration between 10 and 200 mg/l. The degradation products were identified by comparison to oligosaccharide standards (10-200 mg $L^{-1}$ each) as listed above.

Analysis of the hydrolysates by TLC was used for quick analysis of multiple samples in parallel. TLC was performed using silica gel 60 plates from Merck Millipore GmbH (Düsseldorf, Germany) as stationary and acetonitrile-water 8:2 v/v as mobile phase. For staining, the plates were sprayed with 5 mL staining solution (100 mL acetone, 1 g diphenylamine, 1 mL anilin) with 0.5 mL 85% freshly added phosphoric acid. Spraying was done using the DESAGA ChromaJet DS 20 from Sarstedt (Nuermbrecht, Germany). Subsequently, the plates were developed for 20 min at 120° C. The applied volume for each hydrolysate and negative control was 4.5 μL and 1 microL of a 1 microg/μL stock solution for each analyte.

Quantification was performed using a XGOS standard mixture from Megazyme with 0.4 g/L, 0.2 g/L, 0.1 g/L, and 0.05 g/L.

Results: In contrast to the prior art (WO1991011112) enzymatic TKP (20% wt/vol) hydrolysis to the maximum DP7-DP9 amounts is achieved by 0.65% (wt/wt TKP) in less than 1 hour using SEQ ID NO 3 (FIG. 9). Another results was obtained by using SEQ ID NO 2 enzyme concentration below 0.03% (wt/wt TKP) which is sufficient to hydrolyze TKP (20% wt/vol) to DP7-DP9 oligosaccharides completely within 24 h (FIG. 8). Further reduction of SEQ ID NO 3 enzyme concentration to 0.006% (wt/wt TKP) leads to a sufficient hydrolysis over 80% within 24 hours (FIG. 8).

Example 8: Peak Area Determination

20% (wt/wt) TKP was hydrolyzed for 24 hours with 3% (wt/wt TKP) SEQ ID NO 3 in accordance with example 3. Samples were taken after 15 min, 30 min, 45 min, 1 h, 2 h, 3 h, 4 h, 8 h, and 24 h and analyzed using HPAEC-PAD described in example 7. Peak areas (nC*min) for the produced oligosaccharides were determined for DP7, DP8 and DP9 oligosaccharides separately and the percentage of each oligosaccharide was determined.

Result: Once the TKP is hydrolyzed completely the ratio between the DP7, DP8 and DP9 oligosaccharides is is stable and does not change with prolonged reaction times. In contrast to the prior art (WO1991011112) we do not observe any further oligosaccharide degradation causing unwanted monosaccharides or loss of XGOS yield (FIG. 10). Even using a very high enzyme concentration (3%) and complete TKP hydrolysis reached after less than an hour the ratio between DP 7, 8 and 9 oligosaccharides is stable over time (FIG. 10).

Example 9: Detection of Monosaccharides

The polysaccharide xyloglucan has a backbone of beta1→4-linked glucose residues, most of which are substituted with 1,6 linked xylose sidechains. The xylose residues are in many cases decorated with galactose. To analyze possible further xyloglucan hydrolysis to monosaccharides we specifically analyzed the content of monomeric glucose and galactose after enzymatic hydrolysis.

Residual galactose in XGOS powder was determined using a Lactose/D-Galactose detection kit as described by the manufacturer (Megazyme, Ireland). Measurement was performed with a Perkin Elmer Lambda 35 UV/Vis spectrophotometer at 340 nm. A 20% (wt/vol) purified XGOS solution, whereby the XGOS was produced as described in example 3 and purified as described in example 6 with 0.05% SEQ ID NO 3, was used to determine the galactose concentration. The galactose concentration in the XGOS solution was determined by inferring the galactose concentration from a standard curve prepared with galactose. The apparent galactose content in the preparation was 72 ppm.

Residual glucose in the XGOS preparation was determined using a coupled enzymatic assay, with *Aspergillus niger* glucose oxidase (Type VII, Sigma Aldrich) and horseradish peroxidase (type VI, Sigma Aldrich) as described by (Kovacevic et al. 2014). The assay was performed in 0.1 M sodium acetate buffer pH 5.5 containing 2 mM ABTS, 1.3 U/mL glucose oxidase and 0.5 U/mL horseradish peroxidase using a 20% (wt/vol) purified XGOS solution as sample. Change of absorbance at 410 nm was followed in a Tecan Sunrise microplate reader. No glucose was detected in the 20% (wt/vol) purified XGOS solution. Control experiment: Through addition of glucose to the same TKP solution the minimal detectable glucose concentration in the 20% (wt/vol) purified XGOS solution was determined to be 54 ppm. Hence residual glucose content in the XGOS preparation is below 54 ppm.

In contrast to the prior art (WO1991011112) the described hydrolysis using enzymes SEQ ID NOs 1-4 process does not produce monosaccharides.

Example 10: Metabolic Stability XGOS

Metabolic stability of the oligosaccharide was assessed using the integrated total dietary fiber assay kit (Megazyme, Ireland). XGOS samples were digested with enzymes as described in AOAC Method 2011.25 and oligosaccharide composition was analyzed after enzymatic treatment as described in example 7 using HPAEC-PAD. Xyloglucan oligosaccharides were resistant to hydrolysis by porcine pancreatic amylase and amyloglucosidase, qualifying XGOS as soluble dietary fiber.

Example 11: Water Content aW-Value

The water activity (aw value) was determined using a AW device from Sprint from Novasina (Lachen, Switzerland) at 25° C. The water content of oligosaccharide purified without ethanol precipitation was 0.311. The aw XGOS value prepared including ethanol precipitation was 0.327.

Example 12: XGOS Stability Against Acid Treatment

For food and feed products, acid stability is necessary. To test the stability of DP7-DP9 XGOS toward acids, 10% (wt/vol) XGOS were solved in water (pH 7.0), incubated for 2 h at 37° C. and compared to the same amount of XGOS treated with 10 mM HCl (pH 2.0) and incubated at the same conditions. The analysis was performed by HPAEC-PAD. There were no differences in oligosaccharide composition between the pH 7.0 and pH 2.0 samples observed.

Example 13: XGOS Stability Against Heat

For pelleting, extruding or pasteurization processes, heat stability is necessary. To test the stability of DP7-DP9 XGOS toward heat 10% (wt/vol) XGOS were solved in water (pH 7.0), incubated for 10 min at 97° C. and compared to the same amount of untreated XGOS. The analysis was performed by HPAEC-PAD. After heat treatment a light precipitation was observed, which didn't affect XGOS solubility. Heat treatment didn't alter the composition of DP7-DP9 XGOS and equal amounts of XGOS were detected in heat treated and non-treated samples. No increase of mono- or disaccharides could be detected. The 10% (wt/vol) XGOS solution was incubated for 20 min at 121° C. and 2 bar and more than 80% XGOS were left in the supernatant. The XGOS composition was not altered. Furthermore, the monomer fraction did not increase.

REFERENCES

Brockmeier, U., Caspers, M., Freudl, R., Jockwer, A., Noll, T., Eggert, T (2006). Systematic Screening of All Signal Peptides from *Bacillus subtilis*: A Powerful Strategy in Optimizing Heterologous Protein Secretion in Gram-positive Bacteria, Journal of Molecular Biology. Volume 362, Issue 3, Pages 393-402.

Fry, S. C., York, W. S., Albersheim, P., Darvill, A., Hayashi, T., Joseleau, J. P., Kato, Y., Lorences, E. P., Maclachlan, G. A., McNeil, M., Mort, A. J., Reid, J. S. G., Seitz, H. U., Selvendran, R. R., Voragen, A. G. J. & White, A. R. (1993). An unambiguous nomenclature for xyloglucan-derived oligosaccharides. Physiol. Plant, 89, 1-3.

Gibson, G. R., Loo, J. V., Rastall, R. A., Roberfroid, M. B. Dietary modulation of the human colonic microbiota: updating the concept of prebiotics. 2004. Nutrition Research Reviews, 17: 259-275.

Hartemink, R., Van Laere, K. M. J., Mertens, A. K. C. and Rombouts, F. M. Fermentation of Xyloglucan by Intestinal Bacteria. Anaerobe (1996). 2, 223-230.

Hawskworth, D. L., Kirk, P. M., Sutton, B. C., Pegler, D. N. Dictionary of the fungi, 8th edn. 1995. CAB International, Wallingford, UK.

Hoy, M. K., Goldman, J. D. Fiber intake of the U.S. population: What We Eat in America, NHANES 2009-2010. Food Surveys Research Group Dietary Data Brief No. 12. September 2014.

Koeck, D. E., Mechelke, M., Zverlov, V. V., Liebl, W., Schwarz, W. H. (2016) *Herbivorax saccincola* gen. nov., sp. nov., a cellulolytic, anaerobic, thermophilic bacterium isolated via in sacco enrichments from a lab scale biogas reactor. International Journal of Systematic and Evolutionary Microbiolog. 66: 4458-4463.

Kumar, C. S., Bhattacharya, S. (2008) Tamarind seed: properties, processing and utilization. Crit Rev Food Sci Nutr. 48(1):1-20.

Larsbrink, J., Rogers, T. E., Hemsworth, G. R., McKee, L. S., Tauzin, A. S., Spadiut, O., Klinter, S., Pudlo, N. A., Urs, K., Koropatkin, N. M., Creagh, A. L., Haynes, C. A., Kelly, A. G., Nilsson Cederholm, S., Davies, G. D., Martens, E. C. and Brumer, H. A discrete genetic locus confers xyloglucan metabolism in select human gut Bacteroidetes. 2014. Nature 499, vol. 506.

Lengeler, J. W., Drews, G., Schlegel, H. G.: Biology of Prokaryotes, Georg Thieme Verlag, Stuttgart. McCleary, B. V. (1980). New chromogenic substrates for the assay of alpha-amylase and (1-4)-β-D-glucanase. Carbohydr. Res., 86, 97-104.

Mangan, D., Liadova, A., Ivory, R. & McCleary, B. V. (2016). Novel approaches to the automated assay of β-glucanase and lichenase activity. Carbohydr. Res. 435, 162-172.

Rao and Srivastava, "Tamarind" in Industrial Gums. R. L. Whistler and J. H. Bemiller, eds., 1973, pp. 402-407.

Scientific Opinion on Dietary Reference Values for carbohydrates and dietary fibrel. EFSA Journal 2010; 8(3):1462

Scientific Opinion on the substantiation of a health claim related to non-digestible carbohydrates and a reduction of post-prandial glycaemic responses pursuant to Article 13(5) of Regulation (EC) No 1924/2006. EFSA Journal 2014; 12(1):3513.

Scientific Opinion on the substantiation of a health claim related to AlphaGOS® and a reduction of post-prandial glycaemic responses pursuant to Article 13(5) of Regulation (EC) No 1924/2006. EFSA Journal 2014; 12(10): 3838.

Simonen, M. and Palva, I. Protein secretion in *Bacillus* species. 1993. Microbiological Reviews 57: 109-137.

Vincken, J.-P., Beldman, G., Messen, W. M. A., Voragen, A. G. J. (1996). Degradation of apple fruit xyloglucan by endoglucanase. Carbohydr. Polym., 29, 75-85.

Wong, D. D. W. S, Chan V. J., McCormack A. and Batt S. B. (2010). A novel xyloglucan-specific endo-beta-1,4-glucanase: biochemical properties and inhibition studies. Applied Microbiology and Biotechnology. 86(5), 1463-1471.

Wood, T. M.; Bhat, K. M. (1988): Methods for measuring cellulase activities. In: Biomass Part A: Cellulose and Hemicellulose, Bd. 160: Elsevier (Methods in Enzymology), p. 87-112.

Yin, Y. B., Mao, X. Z., Yang, J. C., Chen, X., Mao, F. L., Xu, Y., 2012. dbCAN: a web resource for automated carbohydrate-active enzyme annotation. Nucleic Acids Res 40, W445-W451.

---

The invention claimed is:

1. A method for producing xyloglucan oligosaccharides (XGOS) from a xyloglucan source, said method comprising: contacting, at a temperature in the range of 50.5° C. to 80° C., a xyloglucan polysaccharide with an enzyme that is a polypeptide selected from the group consisting of SEQ ID NO: 2, SEQ ID NO: 3, and SEQ ID NO: 4, wherein the enzyme exhibits xyloglucanase activity at a temperature higher than 50° C., and exhibits an end product inhibition constant (Ki) of at least 5 mM.

2. The method of claim 1, wherein the xyloglucan source is selected from the group consisting of peppergrass, rapeseed, apple, bilberry, blueberry, olives, tamarind or fractions thereof comprising tamarind kernel powder, defatted tamarind kernel powder and tamarind seeds.

3. The method according to claim 1, wherein said enzyme is recombinantly produced in a host cell selected from the group consisting of E. coli, Bacillus subtilis and Bacillus licheniformis.

4. The method according to claim 1, wherein the xyloglucan polysaccharide is hydrolyzed in an aqueous solution.

5. The method according to claim 4, further comprising one or more steps of:
removing solids from the solution;
removing proteins and salts from the solution;
removing coloring agents from the solution; and
recovering the xyloglucan source polysaccharide hydrolysate from the solution.

6. The method according to claim 1, wherein said enzyme is present in an amount of 0.005 to 0.03% (w/w) of the xyloglucan source.

7. The method according to claim 1, wherein a xyloglucan hydrolysate is produced that comprises a mixture of DP7 to DP9 XGOS.

8. The method according to claim 1, wherein the amount of the xyloglucan source used is 100 g/l to 750 g/l.

* * * * *

SEQUENCE LISTING

```
<160> NUMBER OF SEQ ID NOS: 14

<210> SEQ ID NO 1
<211> LENGTH: 608
<212> TYPE: PRT
<213> ORGANISM: Clostridium thermocellum

<400> SEQUENCE: 1

Ala Lys Ile Thr Glu Asn Tyr Gln Phe Asp Ser Arg Ile Arg Leu Asn
1               5                   10                  15

Ser Ile Gly Phe Ile Pro Asn His Ser Lys Lys Ala Thr Ile Ala Ala
            20                  25                  30

Asn Cys Ser Thr Phe Tyr Val Val Lys Glu Asp Gly Thr Ile Val Tyr
        35                  40                  45

Thr Gly Thr Ala Thr Ser Met Phe Asp Asn Asp Thr Lys Glu Thr Val
    50                  55                  60

Tyr Ile Ala Asp Phe Ser Ser Val Asn Glu Glu Gly Thr Tyr Tyr Leu
65                  70                  75                  80

Ala Val Pro Gly Val Gly Lys Ser Val Asn Phe Lys Ile Ala Met Asn
                85                  90                  95

Val Tyr Glu Asp Ala Phe Lys Thr Ala Met Leu Gly Met Tyr Leu Leu
            100                 105                 110
```

```
Arg Cys Gly Thr Ser Val Ser Ala Thr Tyr Asn Gly Ile His Tyr Ser
            115                 120                 125

His Gly Pro Cys His Thr Asn Asp Ala Tyr Leu Asp Tyr Ile Asn Gly
        130                 135                 140

Gln His Thr Lys Lys Asp Ser Thr Lys Gly Trp His Asp Ala Gly Asp
145                 150                 155                 160

Tyr Asn Lys Tyr Val Val Asn Ala Gly Ile Thr Val Gly Ser Met Phe
                165                 170                 175

Leu Ala Trp Glu His Phe Lys Asp Gln Leu Glu Pro Val Ala Leu Glu
            180                 185                 190

Ile Pro Glu Lys Asn Asn Ser Ile Pro Asp Phe Leu Asp Glu Leu Lys
        195                 200                 205

Tyr Glu Ile Asp Trp Ile Leu Thr Met Gln Tyr Pro Asp Gly Ser Gly
    210                 215                 220

Arg Val Ala His Lys Val Ser Thr Arg Asn Phe Gly Gly Phe Ile Met
225                 230                 235                 240

Pro Glu Asn Glu His Asp Glu Arg Phe Phe Val Pro Trp Ser Ser Ala
                245                 250                 255

Ala Thr Ala Asp Phe Val Ala Met Thr Ala Met Ala Ala Arg Ile Phe
            260                 265                 270

Arg Pro Tyr Asp Pro Gln Tyr Ala Glu Lys Cys Ile Asn Ala Ala Lys
        275                 280                 285

Val Ser Tyr Glu Phe Leu Lys Asn Asn Pro Ala Asn Val Phe Ala Asn
    290                 295                 300

Gln Ser Gly Phe Ser Thr Gly Glu Tyr Ala Thr Val Ser Asp Ala Asp
305                 310                 315                 320

Asp Arg Leu Trp Ala Ala Ala Glu Met Trp Glu Thr Leu Gly Asp Glu
                325                 330                 335

Glu Tyr Leu Arg Asp Phe Glu Asn Arg Ala Ala Gln Phe Ser Lys Lys
            340                 345                 350

Ile Glu Ala Asp Phe Asp Trp Asp Asn Val Ala Asn Leu Gly Met Phe
        355                 360                 365

Thr Tyr Leu Leu Ser Glu Arg Pro Gly Lys Asn Pro Ala Leu Val Gln
    370                 375                 380

Ser Ile Lys Asp Ser Leu Leu Ser Thr Ala Asp Ser Ile Val Arg Thr
385                 390                 395                 400

Ser Gln Asn His Gly Tyr Gly Arg Thr Leu Gly Thr Thr Tyr Tyr Trp
                405                 410                 415

Gly Cys Asn Gly Thr Val Val Arg Gln Thr Met Ile Leu Gln Val Ala
            420                 425                 430

Asn Lys Ile Ser Pro Asn Asn Asp Tyr Val Asn Ala Ala Leu Asp Ala
        435                 440                 445

Ile Ser His Val Phe Gly Arg Asn Tyr Asn Arg Ser Tyr Val Thr
    450                 455                 460

Gly Leu Gly Ile Asn Pro Met Asn Pro His Asp Arg Arg Ser Gly
465                 470                 475                 480

Ala Asp Gly Ile Trp Glu Pro Trp Pro Gly Tyr Leu Val Gly Gly
                485                 490                 495

Trp Pro Gly Pro Lys Asp Trp Val Asp Ile Gln Asp Ser Tyr Gln Thr
            500                 505                 510

Asn Glu Ile Ala Ile Asn Trp Asn Ala Ala Leu Ile Tyr Ala Leu Ala
        515                 520                 525
```

```
Gly Phe Val Asn Tyr Asn Ser Ala Gln Asn Glu Val Leu Tyr Gly Asp
            530                 535                 540

Val Asn Asp Asp Gly Lys Val Asn Ser Thr Asp Leu Thr Leu Leu Lys
545                 550                 555                 560

Arg Tyr Val Leu Lys Ala Val Ser Thr Leu Pro Ser Ser Lys Ala Glu
                565                 570                 575

Lys Asn Ala Asp Val Asn Arg Asp Gly Arg Val Asn Ser Ser Asp Val
                580                 585                 590

Thr Ile Leu Ser Arg Tyr Leu Ile Arg Val Ile Glu Lys Leu Pro Ile
            595                 600                 605

<210> SEQ ID NO 2
<211> LENGTH: 433
<212> TYPE: PRT
<213> ORGANISM: Herbivorax saccincola

<400> SEQUENCE: 2

Ser Thr Ala Tyr Thr Gly Met Arg Asp Ile Thr Ser Leu Glu Leu Val
1               5                   10                  15

Asn Glu Met Arg Ile Gly Trp Asn Leu Gly Asn Thr Leu Asp Ala Ile
            20                  25                  30

Gly Gly Glu Thr Asn Trp Gly Asn Pro Lys Thr Thr Lys Glu Met Ile
        35                  40                  45

Asp Lys Val Lys Glu Met Gly Phe Asn Thr Val Arg Phe Pro Val Thr
50                  55                  60

Trp Gly His Val Gly Pro Ala Pro Asp Tyr Lys Ile Asp Glu Gly
65                  70                  75                  80

Trp Leu Asn Arg Val Glu Val Val Asn Tyr Ala Leu Ser Asn Asp
                85                  90                  95

Met Tyr Ala Ile Ile Asn Leu His His Glu Asn Ser Trp Leu Val Pro
            100                 105                 110

Thr Tyr Ala Gln Glu Lys Arg Ser Thr Glu Gln Leu Val Lys Ile Trp
        115                 120                 125

Glu Gln Val Ala Thr Arg Phe Lys Asp Tyr Gly Asp Tyr Leu Ile Phe
130                 135                 140

Glu Thr Met Asn Glu Pro Arg Val Glu Asn Ser Pro Tyr Glu Trp Ser
145                 150                 155                 160

Gly Gly Thr Pro Glu Asn Arg His Val Ile Asn Asn Phe Asn Leu Ala
                165                 170                 175

Ala Val Asn Thr Ile Arg Ser Thr Gly Gly Asn Asn Ala Lys Arg His
            180                 185                 190

Ile Met Ile Pro Ala His Ala Ala Ser Ala Ile Asp Ile Ala Leu Asn
        195                 200                 205

Asp Leu Val Ile Pro Asn Asn Asp Arg Ile Ile Ile Ser Val His
    210                 215                 220

Asn Tyr Ser Pro Tyr Phe Phe Ala Met Asp Val Asn Gly Thr Ala Ser
225                 230                 235                 240

Trp Gly Ser Asp Tyr Asp Lys Ala Ser Leu Ala Ala Glu Leu Glu Ala
                245                 250                 255

Leu Tyr Asn Arg Phe Ile Lys Asn Gly Arg Ala Val Val Ile Gly Glu
            260                 265                 270

Phe Gly Ser Ile Asn Lys Asn Asn Leu Ser Asp Arg Ile Arg His Ala
        275                 280                 285

Glu Phe Phe Ala Lys Glu Ala Arg Lys Arg Gly Ile Thr Val Ile Trp
290                 295                 300
```

Trp Asp Asn Gly Tyr Asn Glu Gly Gly Lys Ala Glu Ser Tyr Ala Leu
305                 310                 315                 320

Leu Asp Arg Arg Asn Leu Thr Trp Tyr His Pro Glu Ile Ala Glu Ala
            325                 330                 335

Leu Val Arg Gly Ala Gly Val Pro Glu Pro Thr Pro Thr Pro Thr
            340                 345                 350

Pro Glu Pro Thr Pro Ser Pro Gly Glu Asp Ile Leu Tyr Gly Asp Leu
        355                 360                 365

Asn Gly Asp Gly Ile Ile Asn Ser Ile Asp Tyr Asn Leu Leu Asn Arg
    370                 375                 380

Tyr Ile Leu Glu Val Ile Asp Asp Leu Pro Val Glu Asn Tyr Ser Lys
385                 390                 395                 400

Val Ala Asp Leu Asn Gly Asp Gly Val Ile Asn Ser Asn Asp Ala Val
                405                 410                 415

Leu Leu Gly Arg Phe Ile Leu Glu Ile Val Asp Lys Phe Pro Val Asp
            420                 425                 430

Lys

<210> SEQ ID NO 3
<211> LENGTH: 534
<212> TYPE: PRT
<213> ORGANISM: Artificial sequence
<220> FEATURE:
<223> OTHER INFORMATION: Recombinat polypeptide

<400> SEQUENCE: 3

Ala Lys Ile Thr Glu Asn Tyr Gln Phe Asp Ser Arg Ile Arg Leu Asn
1               5                   10                  15

Ser Ile Gly Phe Ile Pro Asn His Ser Lys Lys Ala Thr Ile Ala Ala
            20                  25                  30

Asn Cys Ser Thr Phe Tyr Val Val Lys Glu Asp Gly Thr Ile Val Tyr
        35                  40                  45

Thr Gly Thr Ala Thr Ser Met Phe Asp Asn Asp Thr Lys Glu Thr Val
    50                  55                  60

Tyr Ile Ala Asp Phe Ser Ser Val Asn Glu Glu Gly Tyr Tyr Leu
65                  70                  75                  80

Ala Val Pro Gly Val Gly Lys Ser Val Asn Phe Lys Ile Ala Met Asn
                85                  90                  95

Val Tyr Glu Asp Ala Phe Lys Thr Ala Met Leu Gly Met Tyr Leu Leu
            100                 105                 110

Arg Cys Gly Thr Ser Val Ser Ala Thr Tyr Asn Gly Ile His Tyr Ser
        115                 120                 125

His Gly Pro Cys His Thr Asn Asp Ala Tyr Leu Asp Tyr Ile Asn Gly
    130                 135                 140

Gln His Thr Lys Lys Asp Ser Thr Lys Gly Trp His Asp Ala Gly Asp
145                 150                 155                 160

Tyr Asn Lys Tyr Val Val Asn Ala Gly Ile Thr Val Gly Ser Met Phe
                165                 170                 175

Leu Ala Trp Glu His Phe Lys Asp Gln Leu Glu Pro Val Ala Leu Glu
            180                 185                 190

Ile Pro Glu Lys Asn Asn Ser Ile Pro Asp Phe Leu Asp Glu Leu Lys
        195                 200                 205

Tyr Glu Ile Asp Trp Ile Leu Thr Met Gln Tyr Pro Asp Gly Ser Gly
    210                 215                 220

```
Arg Val Ala His Lys Val Ser Thr Arg Asn Phe Gly Gly Phe Ile Met
225                 230                 235                 240

Pro Glu Asn Glu His Asp Glu Arg Phe Phe Val Pro Trp Ser Ser Ala
            245                 250                 255

Ala Thr Ala Asp Phe Val Ala Met Thr Ala Met Ala Ala Arg Ile Phe
        260                 265                 270

Arg Pro Tyr Asp Pro Gln Tyr Ala Glu Lys Cys Ile Asn Ala Ala Lys
    275                 280                 285

Val Ser Tyr Glu Phe Leu Lys Asn Asn Pro Ala Asn Val Phe Ala Asn
290                 295                 300

Gln Ser Gly Phe Ser Thr Gly Glu Tyr Ala Thr Val Ser Asp Ala Asp
305                 310                 315                 320

Asp Arg Leu Trp Ala Ala Glu Met Trp Glu Thr Leu Gly Asp Glu
            325                 330                 335

Glu Tyr Leu Arg Asp Phe Glu Asn Arg Ala Ala Gln Phe Ser Lys Lys
            340                 345                 350

Ile Glu Ala Asp Phe Asp Trp Asp Asn Val Ala Asn Leu Gly Met Phe
            355                 360                 365

Thr Tyr Leu Leu Ser Glu Arg Pro Gly Lys Asn Pro Ala Leu Val Gln
370                 375                 380

Ser Ile Lys Asp Ser Leu Leu Ser Thr Ala Asp Ser Ile Val Arg Thr
385                 390                 395                 400

Ser Gln Asn His Gly Tyr Gly Arg Thr Leu Gly Thr Thr Tyr Tyr Trp
            405                 410                 415

Gly Cys Asn Gly Thr Val Val Arg Gln Thr Met Ile Leu Gln Val Ala
            420                 425                 430

Asn Lys Ile Ser Pro Asn Asn Asp Tyr Val Asn Ala Ala Leu Asp Ala
            435                 440                 445

Ile Ser His Val Phe Gly Arg Asn Tyr Tyr Asn Arg Ser Tyr Val Thr
        450                 455                 460

Gly Leu Gly Ile Asn Pro Pro Met Asn Pro His Asp Arg Arg Ser Gly
465                 470                 475                 480

Ala Asp Gly Ile Trp Glu Pro Trp Pro Gly Tyr Leu Val Gly Gly Gly
            485                 490                 495

Trp Pro Gly Pro Lys Asp Trp Val Asp Ile Gln Asp Ser Tyr Gln Thr
            500                 505                 510

Asn Glu Ile Ala Ile Asn Trp Asn Ala Ala Leu Ile Tyr Ala Leu Ala
            515                 520                 525

Gly Phe Val Asn Tyr Asn
            530

<210> SEQ ID NO 4
<211> LENGTH: 360
<212> TYPE: PRT
<213> ORGANISM: Artificial sequence
<220> FEATURE:
<223> OTHER INFORMATION: Recombinant polypeptide

<400> SEQUENCE: 4

Ser Thr Ala Tyr Thr Gly Met Arg Asp Ile Thr Ser Leu Glu Leu Val
1               5                   10                  15

Asn Glu Met Arg Ile Gly Trp Asn Leu Gly Asn Thr Leu Asp Ala Ile
            20                  25                  30

Gly Gly Glu Thr Asn Trp Gly Asn Pro Lys Thr Thr Lys Glu Met Ile
        35                  40                  45
```

```
Asp Lys Val Lys Glu Met Gly Phe Asn Thr Val Arg Phe Pro Val Thr
 50                  55                  60
Trp Gly Gly His Val Gly Pro Ala Pro Asp Tyr Lys Ile Asp Glu Gly
 65                  70                  75                  80
Trp Leu Asn Arg Val Glu Val Val Asn Tyr Ala Leu Ser Asn Asp
                 85                  90                  95
Met Tyr Ala Ile Ile Asn Leu His His Glu Asn Ser Trp Leu Val Pro
            100                 105                 110
Thr Tyr Ala Gln Glu Lys Arg Ser Thr Glu Gln Leu Val Lys Ile Trp
        115                 120                 125
Glu Gln Val Ala Thr Arg Phe Lys Asp Tyr Gly Asp Tyr Leu Ile Phe
    130                 135                 140
Glu Thr Met Asn Glu Pro Arg Val Glu Asn Ser Pro Tyr Glu Trp Ser
145                 150                 155                 160
Gly Gly Thr Pro Glu Asn Arg His Val Ile Asn Asn Phe Asn Leu Ala
                165                 170                 175
Ala Val Asn Thr Ile Arg Ser Thr Gly Gly Asn Asn Ala Lys Arg His
            180                 185                 190
Ile Met Ile Pro Ala His Ala Ala Ser Ala Ile Asp Ile Ala Leu Asn
        195                 200                 205
Asp Leu Val Ile Pro Asn Asn Asp Arg Ile Ile Ile Ser Val His
    210                 215                 220
Asn Tyr Ser Pro Tyr Phe Phe Ala Met Asp Val Asn Gly Thr Ala Ser
225                 230                 235                 240
Trp Gly Ser Asp Tyr Asp Lys Ala Ser Leu Ala Ala Glu Leu Glu Ala
                245                 250                 255
Leu Tyr Asn Arg Phe Ile Lys Asn Gly Arg Ala Val Val Ile Gly Glu
            260                 265                 270
Phe Gly Ser Ile Asn Lys Asn Asn Leu Ser Asp Arg Ile Arg His Ala
        275                 280                 285
Glu Phe Phe Ala Lys Glu Ala Arg Lys Arg Gly Ile Thr Val Ile Trp
    290                 295                 300
Trp Asp Asn Gly Tyr Asn Glu Gly Gly Lys Ala Glu Ser Tyr Ala Leu
305                 310                 315                 320
Leu Asp Arg Arg Asn Leu Thr Trp Tyr His Pro Glu Ile Ala Glu Ala
                325                 330                 335
Leu Val Arg Gly Ala Gly Gly Val Pro Glu Pro Thr Pro Thr Pro Thr
            340                 345                 350
Pro Glu Pro Thr Pro Ser Pro Gly
        355                 360

<210> SEQ ID NO 5
<211> LENGTH: 31
<212> TYPE: DNA
<213> ORGANISM: Artificial sequence
<220> FEATURE:
<223> OTHER INFORMATION: synthetic oligonucleotide

<400> SEQUENCE: 5
atacatatgg caaaaataac ggagaattat c                           31

<210> SEQ ID NO 6
<211> LENGTH: 26
<212> TYPE: DNA
<213> ORGANISM: Artificial sequence
<220> FEATURE:
<223> OTHER INFORMATION: synthetic oligonucleotide
```

```
<400> SEQUENCE: 6
tggtggtgct cgagattata gttgac                                          26

<210> SEQ ID NO 7
<211> LENGTH: 27
<212> TYPE: DNA
<213> ORGANISM: Artificial sequence
<220> FEATURE:
<223> OTHER INFORMATION: synthetic oligonucleotide

<400> SEQUENCE: 7
tggtgctcga gtattggtaa tttctcg                                         27

<210> SEQ ID NO 8
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 8
ttaagaagga gatatacata tgtctacagc atacacaggt atg                       43

<210> SEQ ID NO 9
<211> LENGTH: 51
<212> TYPE: DNA
<213> ORGANISM: Artificial sequence
<220> FEATURE:
<223> OTHER INFORMATION: synthetic oligonucleotide

<400> SEQUENCE: 9
tcagtggtgg tggtggtggt gctcgagttt atcaacggga aatttatcta c              51

<210> SEQ ID NO 10
<211> LENGTH: 46
<212> TYPE: DNA
<213> ORGANISM: Artificial sequence
<220> FEATURE:
<223> OTHER INFORMATION: synthetic oligonucleotide

<400> SEQUENCE: 10
gatctcagtg gtggtggtgg tggtgcccag gagacggtgt tggctc                    46

<210> SEQ ID NO 11
<211> LENGTH: 1824
<212> TYPE: DNA
<213> ORGANISM: Clostridium thermocellum

<400> SEQUENCE: 11
gcaaaaataa cggagaatta tcaatttgat tcacgaatcc gtttaaactc aataggtttt     60
ataccgaacc acagcaaaaa ggcgactata gctgcaaatt gttcaacctt ttatgttgtt    120
aaagaagacg gaacaatagt gtataccgga acggcaactt caatgtttga caatgataca    180
aaagaaactg tttatattgc tgattttca tctgttaatg aagaaggaac gtactatctt    240
gccgtgccgg gagtaggaaa aagcgtaaac tttaaaattg caatgaatgt atatgaggat    300
gcttttaaaa cagcaatgct gggaatgtat ttgctgcgct cggcaccag tgtgtcggcc     360 acatacaacg gaatacacta ttcccatgga ccgtgccata ctaatgatgc atatcttgat    420
tatataaacg gacagcatac taaaaaagac agtacaaaag ctggcatga tgcgggcgac    480 tacaacaaat atgtggtaaa cgccggcata accgttggtt caatgttcct ggcgtgggag    540
```

```
cattttaaag accagttgga gcctgtggca ttggagattc cgaaaagaa caattcaata      600 ccggattttc ttgatgaatt aaaatatgag atagactgga ttcttaccat gcaatacect      660 gacgggagcg aagggtggc tcataaagtt tcgacaagga actttggcgg ctttatcatg       720
cctgagaacg aacacgacga aagatttttc gtgccctgga gcagtgccgc aacggcagac      780
tttgttgcca tgacggccat ggctgcaaga atattcaggc cttatgatcc tcaaatgct      840 gaaaaatgta aaatgcggc aaagtaagc tatgagtttt tgaagaacaa tcctgcgaat       900 gttttgcaa accagagtgg attctcaaca ggagaatatg ccactgtcag tgatgcagat       960
gacagattgt gggcggcggc tgaaatgtgg gagaccctgg gagatgaaga atacttaga      1020 gattttgaaa cagggcggc gcaattctcg aaaaaaatag aagccgattt tgactgggat     1080
aatgttgcaa acttaggtat gtttacatat cttttgtcag aaagaccggg caagaatcct     1140
gctttggtgc agtcaataaa ggatagtctc ctttccactg cggattcaat tgtgaggacc    1200
agccaaaacc atggctatgg cagaacccctt ggtacaacat attactgggg atgcaacggc    1260
acggttgtaa gacagactat gatacttcag gttgcgaaca agatttcacc caacaatgat    1320
tatgtaaatg ctgctctcga tgcgatttca catgtatttg aagaaacta ttacaacagg    1380 tcttatgtaa caggccttgg tataaatcct cctatgaatc tcatgacag acgttcaggg    1440 gctgacggaa tatgggagcc gtggcccggt taccttgtag gaggggatg gcccggaccg   1500 aaggattggg tggatattca ggacagttat cagaccaatg aaattgctat aaactggaat   1560
gcggcattga tttatgcct tgccggattt gtcaactata attctgctca aaatgaagta    1620
ctgtacggag atgtgaatga tgacggaaaa gtaaactcca ctgacttgac tttgttaaaa    1680 agatatgtte ttaaagccgt ctcaactctg ccttcttcca aagctgaaaa gaacgcagat   1740
gtaaatcgtg acgaaagagt taattccagt gatgtcacaa tacttcaag atatttgata   1800 agggtaatcg agaaattacc aata                                          1824

<210> SEQ ID NO 12
<211> LENGTH: 1299
<212> TYPE: DNA
<213> ORGANISM: Herbivorax saccincola

<400> SEQUENCE: 12
tctacagcat acacaggtat gagggatatt acatctttag aacttgtaaa tgaaatgagg       60
attggatgga atttaggtaa taccccttgat gccattggag gggaaactaa ctggggaaat     120
cctaaaacca caaaggaaat gattgataaa gttaaagaaa tgggctttaa cactgtaagg     180
tttcccgtta cctggggagg tcatgtggga ccggctcccg attataaaat tgatgaaggc    240
tggctgaaca gggtggagga agtagtgaat tatgcacttt caaacgatat gtatgctata    300
attaatcttc accacgaaaa ctcatggctt gttcctacat atgcccagga aaaagaagt   360 acagaacagc tggtgaaaat atgggaacaa gttgcaacce gctttaaaga ctatggtgac    420
tatttaattt ttgaaacgat gaatgaaccc agggtagaaa actcaccctta tgaatggtca   480 ggtggaacac ctgaaaaccg ccatgttata aataatttta atttggctgc tgtaaacaca    540
atcagaagta ccggggggaa caatgcaaaa aggcatataa tgattccggc acatgctgca    600
tctgctatag atattgcatt aaatgacctg gttattccta taatgatga caggataatt   660 atatctgtac ataattattc cccatacttc tttgctatgg atgtcaacgg cactgccagc    720
tggggaagtg attatgacaa ggcttctctt gcagctgaat tggaggcact ttataataga   780
tttattaaaa atggaagagc agttgtcata ggtgagtttg gcagtataaa taagaataac    840
```

-continued

```
ctttcagaca ggatccggca tgcagagttt tttgctaaag aagcaagaaa aagggcata      900 acggtgatat ggtgggataa tggatacaac gagggtggta aagcagaatc ctatgccctt     960
ttagacagaa gaaaccttac atggtaccat cctgagattg cagaggcact tgtaagaggg    1020 gcaggggag taccggagcc aacaccgaca cctactccag agccaacacc gtctcctggg     1080
gaagatattc tgtatgggga tttaaatggg gacggcatta ttaattcaat tgactataat   1140
ttattgaaca ggtatatatt agaagtgata gatgatttgc ctgttgaaaa ttatagtaaa   1200
gtagcagatt taaacggtga tggtgttatt aactcaaatg atgcagtttt gctgggaaga   1260
tttatattgg agattgtaga taaatttccc gttgataaa                          1299
```

<210> SEQ ID NO 13
<211> LENGTH: 1602
<212> TYPE: DNA
<213> ORGANISM: Artificial sequence
<220> FEATURE:
<223> OTHER INFORMATION: recombinant polynucleotide

<400> SEQUENCE: 13

```
gcaaaaataa cggagaatta tcaatttgat tcacgaatcc gtttaaactc aataggtttt     60
ataccgaacc acagcaaaaa ggcgactata gctgcaaatt gttcaacctt ttatgttgtt    120
aaagaagacg gaacaatagt gtataccgga acggcaactt caatgtttga caatgataca    180
aaagaaactg tttatattgc tgattttca tctgttaatg aagaaggaac gtactatctt     240
gccgtgccgg gagtaggaaa aagcgtaaac tttaaaattg caatgaatgt atatgaggat    300
gcttttaaaa cagcaatgct gggaatgtat ttgctgcgct gcggcaccag tgtgtcggcc    360
acatacaacg gaatacacta ttcccatgga ccgtgccata ctaatgatgc atatcttgat    420
tatataaacg gacagcatac taaaaaagac agtacaaaag ctggcatga tgcgggcgac     480 tacaacaaat atgtggtaaa cgccggcata accgttggtt caatgttcct ggcgtgggag    540
cattttaaag accagttgga gcctgtggca ttggagattc ccgaaaagaa caattcaata    600
ccggattttc ttgatgaatt aaaatatgag atagactgga ttcttaccat gcaataccct   660
gacgggagcg aagggtggc tcataaagtt tcgacaagga actttggcgg ctttatcatg     720
cctgagaacg aacacgacga agatttttc gtgccctgga gcagtgccgc aacggcagac    780
tttgttgcca tgacggccat ggctgcaaga atattcaggc cttatgatcc tcaatatgct   840
gaaaaatgta taaatgcggc aaaagtaagc tatgagtttt tgaagaacaa tcctgcgaat   900 gttttttgcaa accagagtgg attctcaaca ggagaatatg ccactgtcag tgatgcagat   960
gacagattgt gggcggcggc tgaaatgtgg gagaccctgg agatgaaga ataccttaga   1020 gattttgaaa cagggcggc gcaattctcg aaaaaaatag aagccgattt tgactgggat   1080
aatgttgcaa acttaggtat gtttacatat cttttgtcag aaagaccggg caagaatcct   1140
gctttggtgc agtcaataaa ggatagtctc ctttccactg cggattcaat tgtgaggacc   1200
agccaaaacc atggctatgg cagaacccct ggtacaacat attactgggg atgcaacggc   1260
acggttgtaa gacagactat gatacttcag gttgcgaaca agatttcacc caacaatgat   1320
tatgtaaatg ctgctctcga tgcgatttca catgtatttg aagaaaacta ttacaacagg   1380
tcttatgtaa caggccttgg tataaatcct cctatgaatc ctcatgacag acgttcaggg   1440
gctgacggaa tatgggagcc gtggcccggt taccttgtag gaggaggatg gcccggaccg   1500
```

-continued

```
aaggattggg tggatattca ggacagttat cagaccaatg aaattgctat aaactggaat      1560
gcggcattga tttatgccct tgccggattt gtcaactata at                        1602

<210> SEQ ID NO 14
<211> LENGTH: 1080
<212> TYPE: DNA
<213> ORGANISM: Artificial sequence
<220> FEATURE:
<223> OTHER INFORMATION: Synthetic polynucleotide

<400> SEQUENCE: 14
tctacagcat acacaggtat gagggatatt acatctttag aacttgtaaa tgaaatgagg       60
attggatgga atttaggtaa taccccttgat gccattggag gggaaactaa ctggggaaat     120
cctaaaacca caaaggaaat gattgataaa gttaaagaaa tgggctttaa cactgtaagg     180
tttcccgtta cctggggagg tcatgtggga ccggctcccg attataaaat tgatgaaggc     240
tggctgaaca gggtggagga agtagtgaat tatgcacttt caaacgatat gtatgctata     300
attaatcttc accacgaaaa ctcatggctt gttcctacat atgcccagga aaaagaagt     360 acagaacagc tggtgaaaat atgggaacaa gttgcaaccc gctttaaaga ctatggtgac     420 tatttaatt ttgaaacgat gaatgaaccc agggtagaaa actcaccctta tgaatggtca    480 ggtggaacac ctgaaaaccg ccatgttata aataatttta atttggctgc tgtaaacaca     540
atcagaagta ccgggggaaa caatgcaaaa aggcatataa tgattccggc acatgctgca     600
tctgctatag atattgcatt aaatgacctg gttattccta ataatgatga caggataatt     660
atatctgtac ataattattc cccatacttc tttgctatgg atgtcaacgg cactgccagc     720
tggggaagtg attatgacaa ggcttctctt gcagctgaat tggaggcact ttataataga     780
tttattaaaa atggaagagc agttgtcata ggtgagtttg gcagtataaa taagaataac     840
ctttcagaca ggatccggca tgcagagttt tttgctaaag aagcaagaaa aagggggcata     900 acggtgatat ggtgggataa tggatacaac gagggtggta aagcagaatc ctatgccctt     960
ttagacagaa gaaaccttac atggtaccat cctgagattg cagaggcact tgtaagaggg    1020 gcaggggggag taccggagcc aacaccgaca cctactccag agccaacacc gtctcctggg   1080
```